(12) United States Patent
Brada et al.

(10) Patent No.: US 10,806,370 B1
(45) Date of Patent: Oct. 20, 2020

(54) MRI SYSTEM AND METHOD FOR DETECTION AND CORRECTION OF PATIENT MOTION

(71) Applicant: GE Precision Healthcare LLC, Wauwatosa, WI (US)

(72) Inventors: Rafael Shmuel Brada, Hod-Hasharon (IL); Christopher Judson Hardy, Schenectady, NY (US); Sangtae Ahn, Guilderland, NY (US); Isabelle Heukensfeldt Jansen, Schenectady, NY (US); Itzik Malkiel, Givatayim (IL); Michael Rotman, Petach-Tikva (IL); Ron Wein, Ramat Hasharon (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1 day.

(21) Appl. No.: 16/394,786

(22) Filed: Apr. 25, 2019

(51) Int. Cl.
*A61B 5/055* (2006.01)
*G01R 33/565* (2006.01)
*G01R 33/56* (2006.01)
*G01R 33/48* (2006.01)
*G16H 30/40* (2018.01)

(52) U.S. Cl.
CPC ........ *A61B 5/0555* (2013.01); *G01R 33/4818* (2013.01); *G01R 33/5608* (2013.01); *G01R 33/56509* (2013.01); *G16H 30/40* (2018.01)

(58) Field of Classification Search
USPC ......................................................... 324/309
See application file for complete search history.

(56) References Cited

U.S. PATENT DOCUMENTS

| 6,329,819 | B1 | 12/2001 | Manduca et al. |
| 7,693,569 | B1* | 4/2010 | Brittain .................. G06T 7/20 600/413 |
| 7,860,291 | B2 | 12/2010 | Hwang |
| 8,306,299 | B2 | 11/2012 | Samsonov et al. |
| 9,714,998 | B2 | 7/2017 | Krueger et al. |
| 2008/0205730 | A1 | 8/2008 | Stehning et al. |
| 2016/0071291 | A1* | 3/2016 | Samsonov ......... G01R 33/5611 600/410 |
| 2017/0219674 | A1 | 8/2017 | Van Der Kouwe et al. |
| 2018/0210058 | A1 | 7/2018 | De Weerdt |

(Continued)

OTHER PUBLICATIONS

Atkinson, et al., "Automatic correction of motion artifacts in magnetic resonance images using an entropy focus criterion," IEEE Transactions on Medical Imaging, vol. 16, Issue:6, pp. 903-910, Dec. 1997.

(Continued)

*Primary Examiner* — Rodney E Fuller
(74) *Attorney, Agent, or Firm* — Fletcher Yoder, P.C.

(57) ABSTRACT

A system and method for detecting, timing, and adapting to patient motion during an MR scan includes using the inconsistencies between calculated images from different coil-array elements to detect the presence of patient motion and, together with the k-space scan-order information, determine the timing of the motion during the scan. Once the timing is known, various actions may be taken, including restarting the scan, reacquiring those portions of k-space acquired before the movement, or correcting for the motion using the existing data and reconstructing a motion-corrected image from the data.

23 Claims, 17 Drawing Sheets

(56) References Cited

U.S. PATENT DOCUMENTS

2018/0356484 A1* 12/2018 Boernert ............ G01R 33/5611
2019/0086501 A1*  3/2019 Bydder .................. G06T 5/001

OTHER PUBLICATIONS

Pipe, James G., "Motion correction with PROPELLER MRI: Application to head motion and free-breathing cardiac imaging," Magnetic Resonance in Medicine, vol. 42 Issue: 5, pp. 963-969, Nov. 1999.

* cited by examiner

US 10,806,370 B1

MRI SYSTEM AND METHOD FOR DETECTION AND CORRECTION OF PATIENT MOTION

BACKGROUND

In general, magnetic resonance imaging (MRI) examinations are based on the interactions among a primary magnetic field, a radiofrequency (RF) magnetic field and time varying magnetic gradient fields with gyromagnetic material having nuclear spins within a subject of interest, such as a patient. Certain gyromagnetic materials, such as hydrogen nuclei in water molecules, have characteristic behaviors in response to external magnetic fields. The precession of spins of these nuclei can be influenced by manipulation of the fields to produce RF signals that can be detected, processed, and used to reconstruct a useful image.

Patient motion is one of the biggest sources of inefficiency in clinical MRI, often requiring re-scans or even second visits by the patient. In particular, patient motion can cause blurriness, artifacts, and other inconsistencies in MR images. Certain approaches to correct motion require either some sort of hardware for monitoring the motion (adding to cost and patient setup time), or navigator sequences (which take time away from the imaging sequence). Accordingly, a need exists for improved methods for data acquisition and reconstruction in magnetic resonance imaging techniques that are sensitive to patient motion.

BRIEF DESCRIPTION

In one embodiment, a magnetic resonance imaging method includes generating intensity-corrected single-coil images from raw magnetic resonance (MR) data of an imaged subject. The raw MR data include data collected by each coil of a plurality of coils in a receiving coil array of an MR system, and the raw MR data are associated with a scan order used during acquisition thereof, the scan order having a plurality of time steps in which k-space is filled in a predetermined manner. The method also includes identifying inconsistencies among the intensity-corrected single-coil images, and calculating, for at least one time step of the scan order, a motion score using the scan order and the inconsistencies to identify timing associated with motion occurring during the acquisition. The method further includes performing a corrective action based at least on the timing associated with the motion to ameliorate the effects of the motion on an MR image produced using at least a portion of the raw MR data.

In another embodiment, a magnetic resonance imaging (MRI) method includes generating intensity-corrected single-coil images from raw magnetic resonance (MR) data of an imaged subject. The raw MR data include data collected by each coil of a plurality of coils in a receiving coil array of an MRI system. The method also includes identifying inconsistencies among the intensity-corrected single-coil images, identifying whether motion occurred during acquisition of the raw MR data based at least on the inconsistencies, and performing further operations of the MRI system in response to determining that motion occurred during the acquisition.

In a further embodiment, a magnetic resonance imaging (MRI) method includes obtaining raw magnetic resonance (MR) data of a subject, wherein the raw MR data include data collected by each coil of a plurality of coils in a receiving coil array of an MRI system. The raw MR data are associated with a scan order used during acquisition thereof, the scan order having a plurality of time steps in which k-space is filled in a predetermined manner. The method also includes using inconsistencies between calculated intensity-corrected single-coil images produced from the raw MR data to detect the presence of motion of the subject and, together with the scan order, determine the timing of the motion during the acquisition. The method further includes performing image reconstruction using the timing of the motion to generate a single motion-corrected image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As set forth above, patient motion is one of the biggest sources of inefficiency in clinical MRI, often requiring re-scans or even second visits by the patient. Research has shown that patient motion can lead to repeated acquisition sequences in as much as 20% of MRI exams. This results in significant annual losses for every scanner as throughput is reduced.

Disclosed embodiments include a system and method for detecting, timing, and adapting to patient motion during or after an MR scan, without the need for external tracking hardware. This uses the inconsistencies between calculated images from different coil-array elements to detect the presence of patient motion and, together with the k-space scan-order information, determines the timing of the motion during the scan. Once the timing is known, various actions can be taken, including restarting the scan, reacquiring those portions of k-space acquired before the movement, or correcting for the motion using the existing data. This correction is done either using a deep-learning neural network or an iterative optimization approach.

Disclosed embodiments also include an adaptive system for detecting patient motion in real time during an MR scan without the need for external monitoring devices or navigation, with the option of adjusting scan parameters to compensate for inconsistent data. Once motion is detected, the system can track multiple separate sub-images to be combined into a motion-free image or can adjust the scan to re-acquire sections of k-space taken before the motion occurred.

Figure 1:
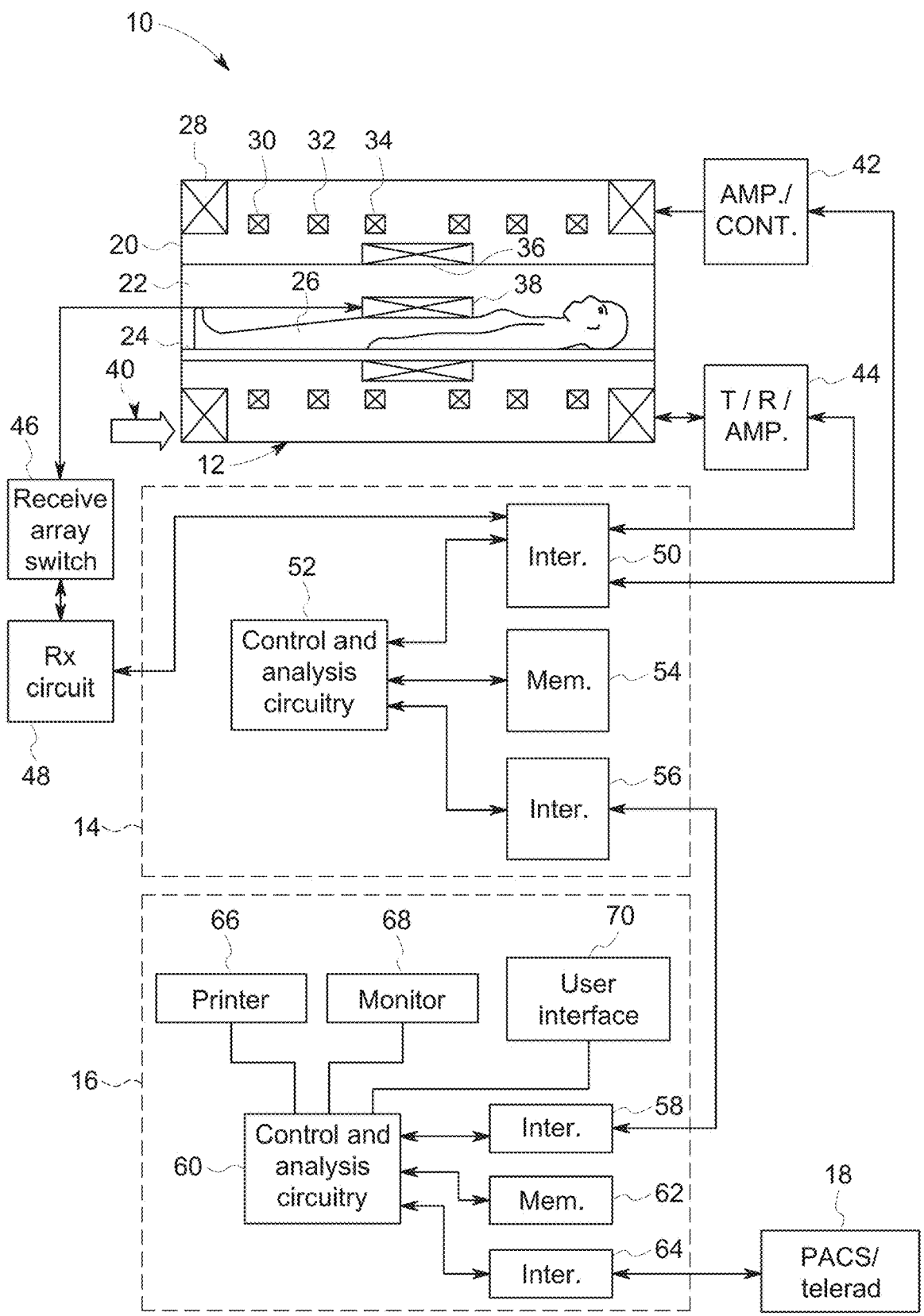
FIG. 1 is a diagrammatic illustration of an embodiment of a magnetic resonance imaging system configured to perform the data acquisition, motion detection and scoring, and image reconstruction described herein.

An example system for performing the techniques described herein is discussed with respect to FIG. 1. The embodiments described herein may be performed by a magnetic resonance imaging (MRI) system, wherein specific imaging routines (e.g., accelerated imaging routines for MRI sequences) are initiated by a user (e.g., a radiologist). Further, the MRI system may perform data acquisition, data correction, and image reconstruction. Accordingly, referring to FIG. 1, a magnetic resonance imaging system 10 is illustrated schematically as including a scanner 12, a scanner control circuit 14, and a system control circuitry 16. According to the embodiments described herein, the MRI system 10 is generally configured to perform MR imaging, such as imaging sequences with adaptive motion correction, various weighting techniques, fluid attenuation techniques, perfusion techniques, tensor imaging, and so on. System 10 additionally includes remote access and storage systems or devices such as picture archiving and communication systems (PACS) 18, or other devices such as teleradiology equipment so that data acquired by the system 10 may be accessed on- or off-site. In this way, acquired data may be acquired, followed by on- or off-site processing and evaluation. While the MRI system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient.

Scanner 12 includes a series of associated coils for producing controlled magnetic fields for exciting the gyromagnetic material within the anatomy of the subject being imaged. Specifically, a primary magnet coil 28 is provided for generating a primary magnetic field generally aligned with the bore 22. A series of gradient coils 30, 32, and 34 permit controlled magnetic gradient fields to be generated for positional encoding of certain of the gyromagnetic nuclei within the patient 26 during examination sequences. A radio frequency (RF) coil 36 is provided, and is configured to generate radio frequency pulses for exciting the certain gyromagnetic nuclei within the patient. In addition to the coils that may be local to the scanner 12, the system 10 also includes a set of receiving coils 38 (e.g., a phased array of coils) configured for placement proximal (e.g., against) the patient 26. The receiving coils 38 may have any geometry, including both enclosed and single-sided geometries. As an example, the receiving coils 38 can include cervical/thoracic/lumbar (CTL) coils, head coils, single-sided spine coils, and so forth. Generally, the receiving coils 38 are placed close to or on top of the patient 26 so as to receive the weak RF signals (weak relative to the transmitted pulses generated by the scanner coils) that are generated by certain of the gyromagnetic nuclei within the patient 26 as they return to their relaxed state. The receiving coils 38 may be switched off so as not to receive or resonate with the transmit pulses generated by the scanner coils, and may be switched on so as to receive or resonate with the RF signals generated by the relaxing gyromagnetic nuclei.

The various coils of system 10 are controlled by external circuitry to generate the desired field and pulses, and to read emissions from the gyromagnetic material in a controlled manner. In the illustrated embodiment, a main power supply 40 provides power to the primary field coil 28. A driver circuit 42 is provided for pulsing the gradient field coils 30, 32, and 34. Such a circuit may include amplification and control circuitry for supplying current to the coils as defined by digitized pulse sequences output by the scanner control circuit 14. Another control circuit 44 is provided for regulating operation of the RF coil 36. Circuit 44 includes a switching device for alternating between the active and inactive modes of operation, wherein the RF coil 36 transmits and does not transmit signals, respectively. Circuit 44 also includes amplification circuitry for generating the RF pulses. Similarly, the receiving coils 38 are connected to switch 46 that is capable of switching the receiving coils 38 between receiving and non-receiving modes such that the receiving coils 38 resonate with the RF signals produced by relaxing gyromagnetic nuclei from within the patient 26 while in the receiving state, and they do not resonate with RF energy from the transmitting coils (i.e., coil 36) so as to prevent undesirable operation while in the non-receiving state. Additionally, a receiving circuit 48 is provided for receiving the data detected by the receiving coils 38, and may include one or more multiplexing and/or amplification circuits.

It should be noted that while the scanner 12 and the control/amplification circuitry described above are illustrated as being coupled by a single line, that many such lines may occur in an actual instantiation. For example, separate lines may be used for control, data communication, and so on. Further, suitable hardware may be disposed along each type of line for the proper handling of the data. Indeed, various filters, digitizers, and processors may be disposed between the scanner and either or both of the scanner and system control circuitry 14, 16. By way of non-limiting example, certain of the control and analysis circuitry described in detail below, although illustrated as a single unit, includes additional hardware such as image reconstruction hardware configured to perform the motion correction and image reconstruction techniques described herein. Further, in certain embodiments, the control and analysis circuitry described herein may be associated with an algorithm used for motion detection and/or another algorithm used for image reconstruction. Indeed, where an algorithm is described in the present disclosure, it should be noted that it may be associated with (e.g., a part of or connected to) the MRI system 10. The algorithm may, for example, be implemented as specific hardware components (e.g., specialized processors), or may be implemented as software (e.g., instructions and/or sets of instructions) on a computing platform.

As illustrated, scanner control circuit 14 includes an interface circuit 50 which outputs signals for driving the gradient field coils and the RF coil and for receiving the data representative of the magnetic resonance signals produced in examination sequences. The interface circuit 50 is coupled to a control and analysis circuit 52. The control and analysis circuit 52 executes the commands for driving the circuit 42 and circuit 44 based on defined protocols selected via system control circuit 16. Control and analysis circuit 52 also serves to receive the magnetic resonance signals and performs subsequent processing before transmitting the data to system control circuit 16. Scanner control circuit 14 also includes one or more memory circuits 54, which store configuration parameters, pulse sequence descriptions, examination results, and so forth, during operation. Interface circuit 56 is coupled to the control and analysis circuit 52 for exchanging data between scanner control circuit 14 and system control circuit 16. Such data will typically include selection of specific examination sequences to be performed, configuration parameters of these sequences, and acquired data, which may be transmitted in raw or processed form from scanner control circuit 14 for subsequent processing, storage, transmission and display. Therefore, in certain embodiments, the control and analysis circuit 52, while illustrated as a single unit, may include one or more hardware devices.

System control circuit 16 includes an interface circuit 58, which receives data from the scanner control circuit 14 and transmits data and commands back to the scanner control circuit 14. The interface circuit 58 is coupled to a control and analysis circuit 60 which may include a CPU in a multi-purpose or application specific computer or workstation. Control and analysis circuit 60 is coupled to a memory circuit 62 to store programming code for operation of the MRI system 10 and to store the processed image data for later reconstruction, display and transmission. The programming code may execute one or more algorithms capable of performing, by way of example, non-Cartesian imaging sequences and processing sampled image data (e.g., blades of data, undersampled data, fluid attenuated data), which will be discussed in detail below. An additional interface circuit 64 may be provided for exchanging image data, configuration parameters, and so forth with external system components such as remote access and storage devices 18. Finally, the system control and analysis circuit 60 may include various peripheral devices for facilitating operator interface and for producing hard copies of the reconstructed images. In the illustrated embodiment, these peripherals include a printer 60, a monitor 62, and user interface 64 including devices such as a keyboard or a mouse.

Scanner 12 and the control and analysis circuit 52 associated therewith produce magnetic fields and radio frequency pulses in a controlled manner to excite and encode specific gyromagnetic material within the patient 26. The scanner 12 and control and analysis circuit 52 also sense the signals emanating from such material and create an image of the material being scanned. In certain embodiments, the scan may include fast spin echo (FSE) scan, gradient echo (GRE) scan sequences, and the like. It should be noted that the MRI system described is merely intended to be exemplary only, and other system types, such as so-called "open" MRI systems may also be used. Similarly, such systems may be rated by the strength of their primary magnet, and any suitably rated system capable of carrying out the data acquisition and processing described below may be employed.

Specifically, aspects of the present disclosure include methods for acquiring magnetic resonance data and processing of such data to construct one or more motion-corrected images. At least a portion of the disclosed methods may be performed by the system 10 described above with respect to FIG. 1. That is, the MRI system 10 may perform the acquisition techniques described herein, and, in some embodiments, the data processing techniques described herein. It should be noted that subsequent to the acquisitions described herein, the system 10 may simply store the acquired data for later access locally and/or remotely, for example in a memory circuit (e.g., memory 62). Thus, when accessed locally and/or remotely, the acquired data may be manipulated by one or more processors contained within an application-specific or general purpose computer. The one or more processors may access the acquired data and execute routines stored on one or more non-transitory, machine readable media collectively storing instructions for performing methods including the motion detection, image processing, and reconstruction methods described herein.

To facilitate presentation of certain of the embodiments described herein, example acquisition and reconstruction sequences are described below. However, the present disclosure is not limited to such acquisitions and sequences, unless explicitly stated otherwise.

In certain embodiments, 2D MR images are generated from Cartesian k-space, using either gradient-echo (GRE) or fast spin echo (FSE) pulse sequences, and acquired with RF receiver coil arrays of 8 or more coils. Each of the coils has a corresponding sensitivity to RF signals generated during acquisition, and the sensitivity of each coil may be mapped to generate sensitivity maps for the coil array. Image reconstruction may involve the generation of a partial image corresponding to each coil by 2D Fourier transformation of the data obtained by a particular coil (referred to as "coil data"), and multiplication by the conjugate of the coil's sensitivity map. To generate a full image, these partial images are summed and the result divided by the sum of squares of the coil sensitivity maps to give the final image.

When a patient moves during the scan, the coil data contain a mixture of Fourier components from two or more motion states. The resulting image is corrupted and contains motion-related artifacts. One aspect of the present disclosure involves detecting the presence of motion and identifying the time during the scan at which it occurred. In accordance with certain embodiments, this motion detection may be performed after the scan has been completed, or may be performed during the scan.

Figure 2:
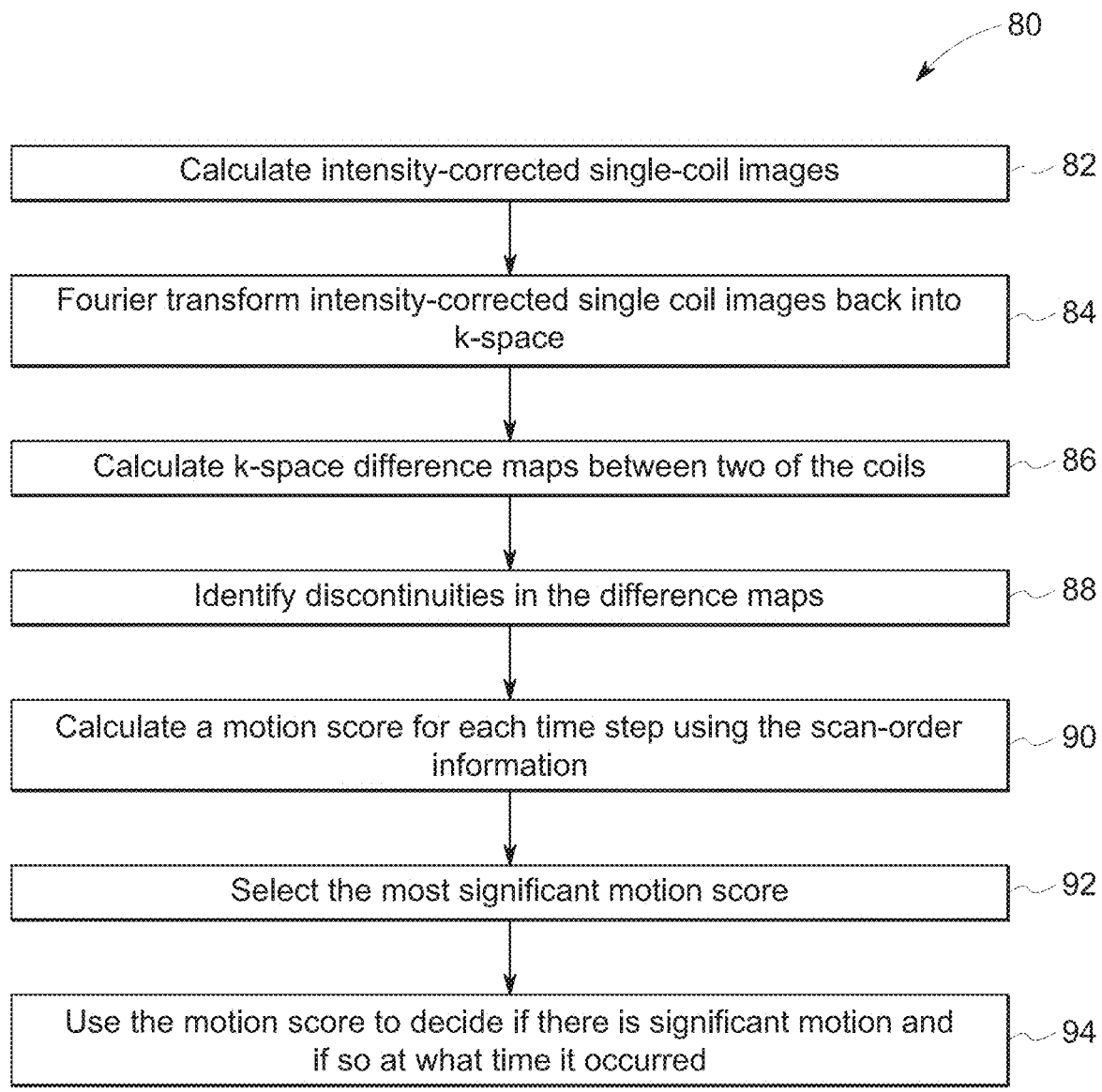
FIG. 2 is a process flow diagram of an embodiment of a method 80 for identifying the occurrence/timing of motion after an MR scan has completed.

FIG. 2 is a process flow diagram of an embodiment of a method 80 for identifying the occurrence/timing of motion, for example after the scan has completed or in other embodiments during a scan. As the method 80 may be performed after the scan has been completed, the method 80 may be performed by the system 10 of FIG. 1, or a remote system having access to the data acquired by system 10. In either case, the method 80 is performed by a general-purpose or application-specific computing system having appropriately configured hardware and software for carrying out the steps described herein. For example, the method 80 may be considered to be performed by a MR motion detection and correction system having processing circuitry and memory circuitry, where the memory circuitry stores instructions (e.g., one or more sets of instructions associated with a software package) that, when performed by the processing circuitry, cause the acts associated with method 80 to be performed. Further, the system that performs method 80 may also include programming to access and/or store the coil data obtained by the system 10 for further processing and analysis. Indeed, the method 80 assumes that a scan has either been performed and completed, or that the scan is underway. In this regard, the method 80, in certain embodiments, may include acts that are not explicitly shown in FIG. 2, such as providing raw magnetic resonance (MR) data. The acts of "providing" such data may include, by way of example, accessing MR data that has already been acquired, performing an acquisition sequence to acquire the MR data using the MRI system 10 of FIG. 1, and so on.

Figure 3:
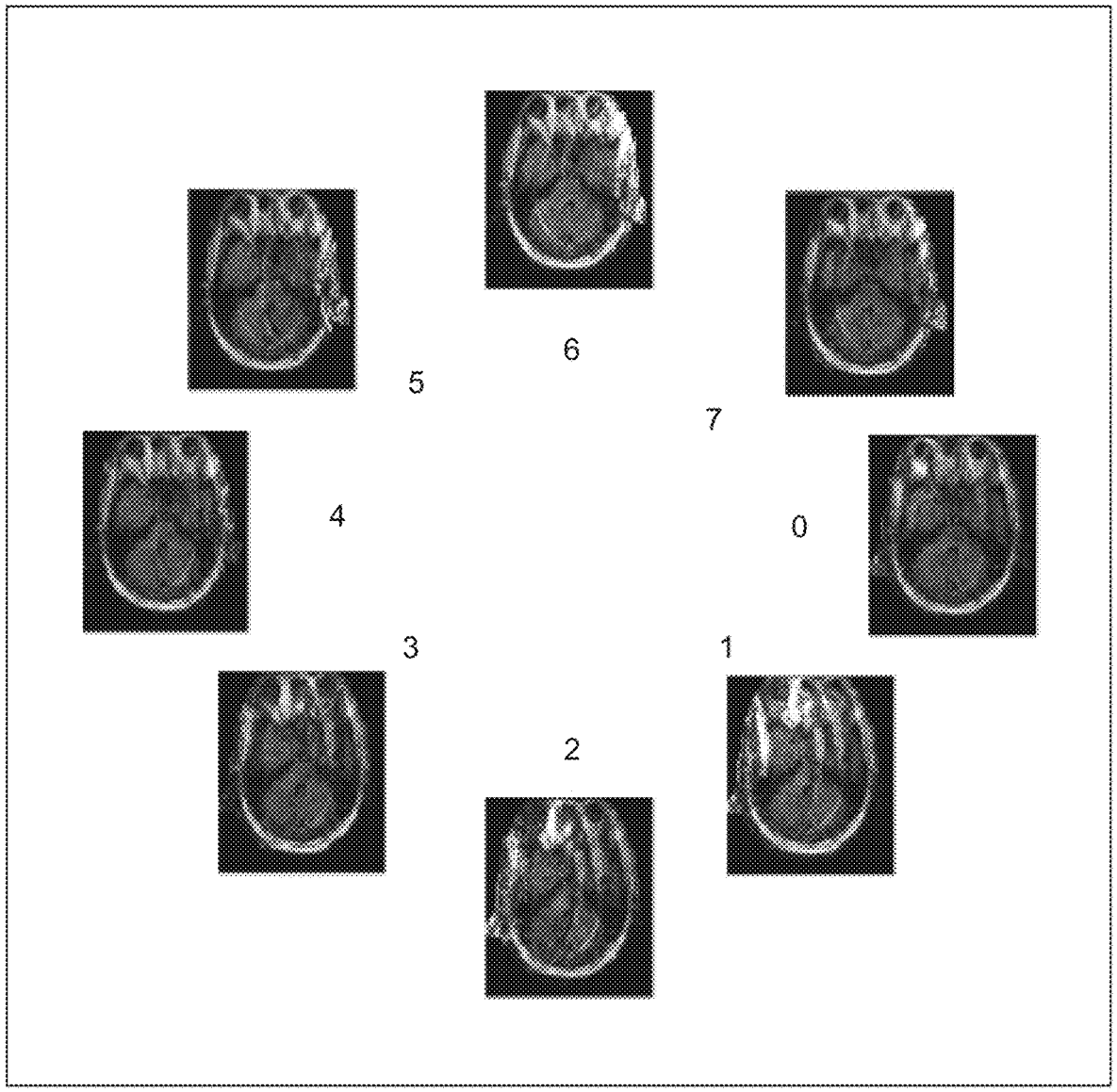
FIG. 3 is a set of example intensity-corrected single-coil images produced during the method of FIG. 2.

As illustrated in FIG. 2, the method 80 includes calculating (block 82) intensity-corrected single-coil images. This may be done, for example, by taking the Inverse Fourier transform of the raw data from each coil in the array, multiplying by the conjugate of the coil sensitivity map, and dividing by the absolute value squared of the coil sensitivity maps. FIG. 3 is a set of example intensity-corrected single-coil images produced by the acts represented by block 82. As shown, each of the images is associated with a particular number corresponding to the coil in the coil array. In this example, the coils are labeled 0-7. The images resulting from the acts of block 82 are complex—including both magnitude and phase, and include motion-related artifacts.

Returning to FIG. 2, once the intensity-corrected single-coil images are generated, motion may be identified based on inconsistencies among the images. Blocks 84-90 detail example processes that are performed to identify the inconsistencies among the images to score the motion and identify timing associated with the motion (e.g., which time steps of the scan order are associated with motion).

Figure 4:
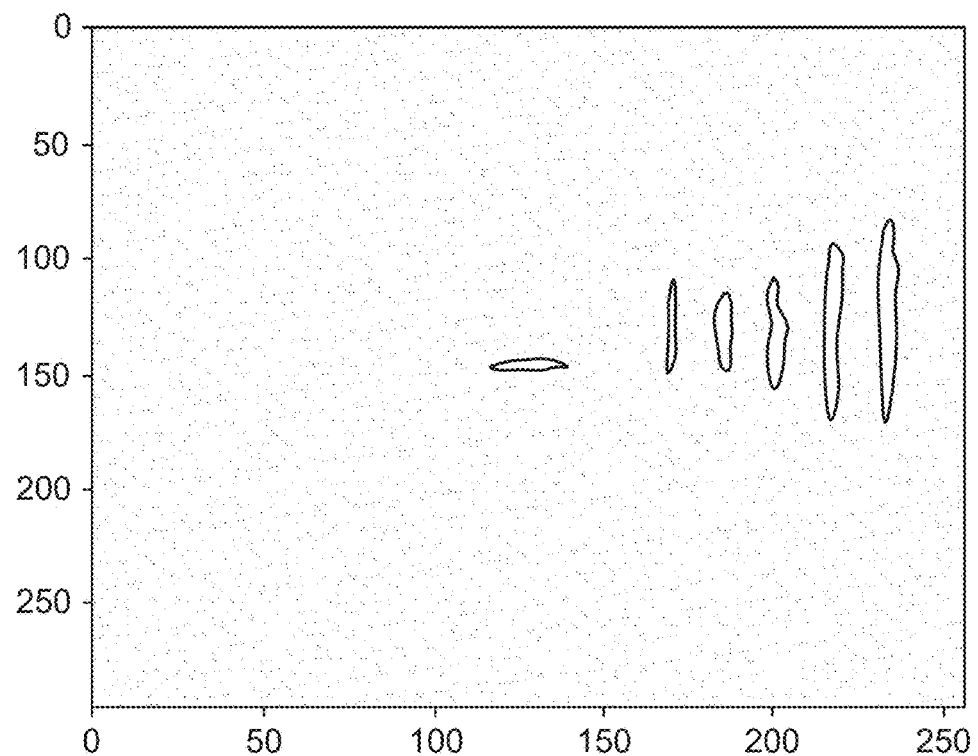
FIG. 4 is a map of the absolute value of the difference between a Fourier transform of two intensity-corrected single-coil images.
Figure 5:
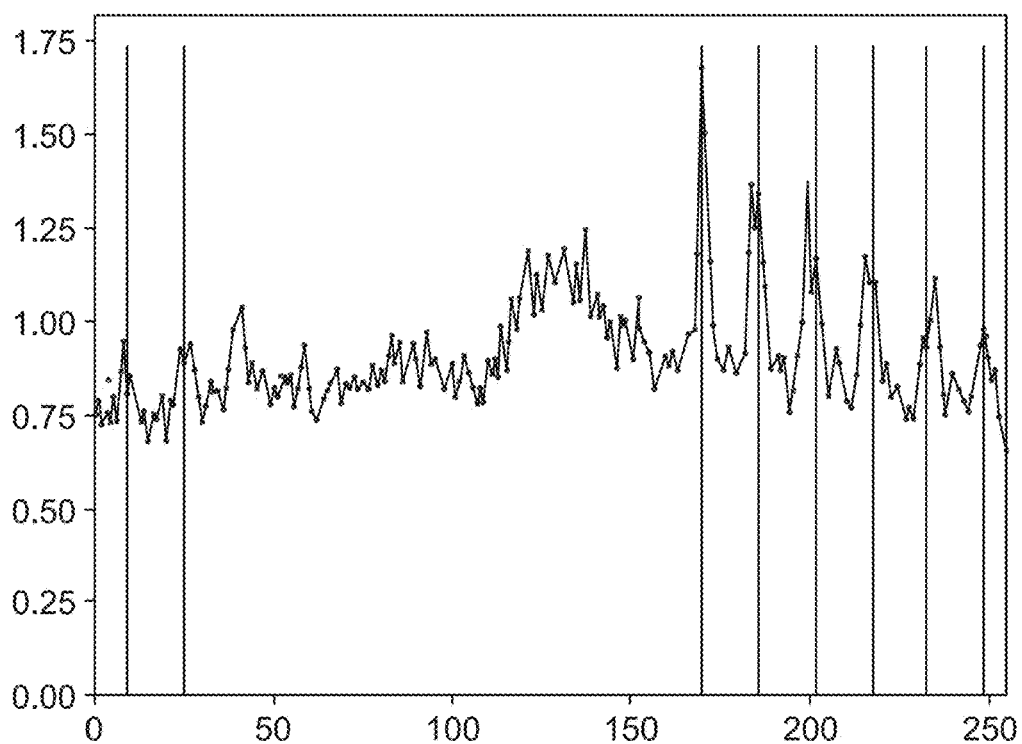
FIG. 5 is a projection of the difference map of FIG. 4 onto an axis.

According to the method 80, a Fourier transform is applied (block 84) to the intensity-corrected single-coil images to transform the data back into k-space. K-space difference maps are then determined (block 86) on a pairwise basis. For example, the acts represented by block 86 may include taking the absolute difference between the Fourier transform (the k-space data) of two intensity-corrected single-coil images. FIG. 4 depicts a map of the absolute value of the difference between the Fourier transform of two intensity-corrected single-coil images. FIG. 5 is a plot of the difference, generated by projection of the difference map along the readout direction onto the x-axis.

Once the difference maps are generated, the method 80 includes identifying (block 88) discontinuities in the difference maps. For example, referring to FIG. 4, discontinuities are visible as bright columns. In this embodiment, the brighter the column, the higher the difference (inconsistency). Referring to FIG. 5, the discontinuities may be visible as large peaks, where the larger the peak, the greater the difference (inconsistency). That is, a size of a peak is proportional to a degree of inconsistency between the k-space data of two intensity-corrected single-coil images.

Figure 6:
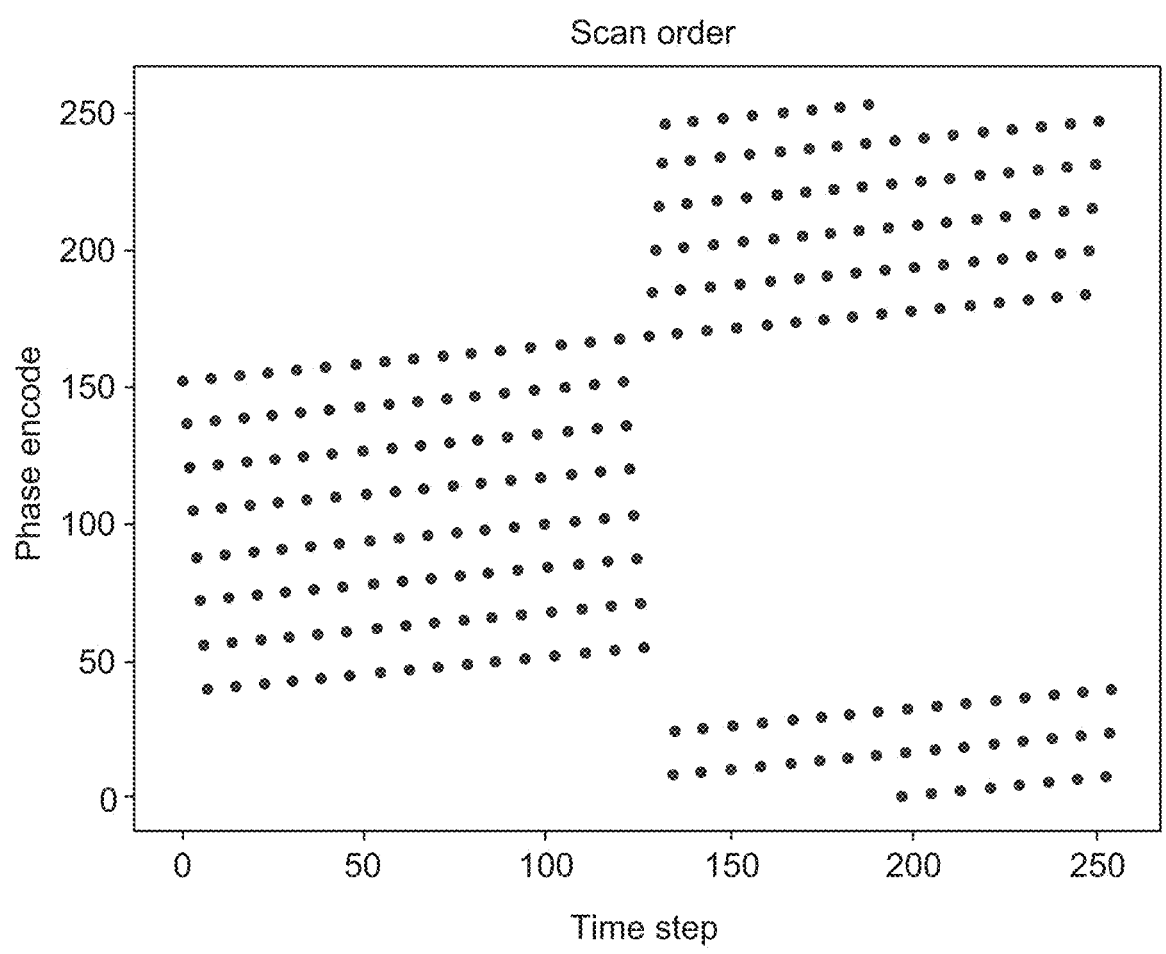
FIG. 6 is an example MRI scan order for a 256×256 FSE image with echo-train length of 8.
Figure 7:
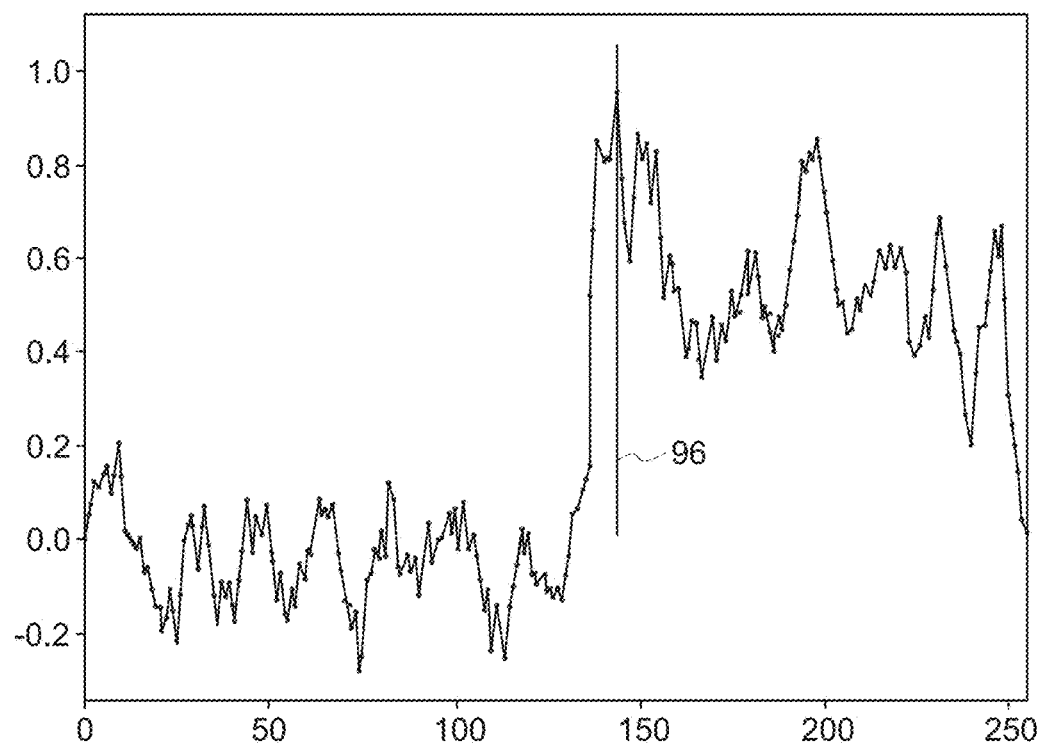
FIG. 7 is an example plot of a motion score calculated for each time step of an image.

Using scan-order information and the difference maps or difference values, a motion score is calculated (block 90) for each time step. FIG. 6 is an example MRI scan order for a 256×256 FSE image with echo-train length of 8. The horizontal axis indicates the scan step in time, and the vertical axis indicates the column, or phase-encode, in Fourier space being scanned at a given time step. In other embodiments, the vertical axis may indicate the row, or phase-encode, in Fourier space being scanned. Note that in this scan order there is a period of 8 before coming back to scanning the adjacent column in k-space. However, the present disclosure is not limited to this example scan order. In general, the elapsed time is not constant between steps. In certain embodiments, the motion score is calculated in accordance with block 90 by taking the integral of the difference, for example by integrating the peaks of the plot of the difference shown in FIG. 5. FIG. 7 is an example plot of a motion score calculated for each time step of an image (a single-coil image). The y-axis is the value of the motion score and the x-axis is the time step.

The most significant motion score is then selected (block 92), for example by selecting the highest motion score. The selected motion score is then used to determine (block 94) whether there is significant motion, and if so, the time at which the motion occurred. By way of example, the calculated motion scores may be compared against a threshold. If the motion score is at or above the threshold, then significant motion may be considered to have occurred. In the plot of FIG. 7, significant motion occurred at time step 144, as shown by line 96.

Figure 8:
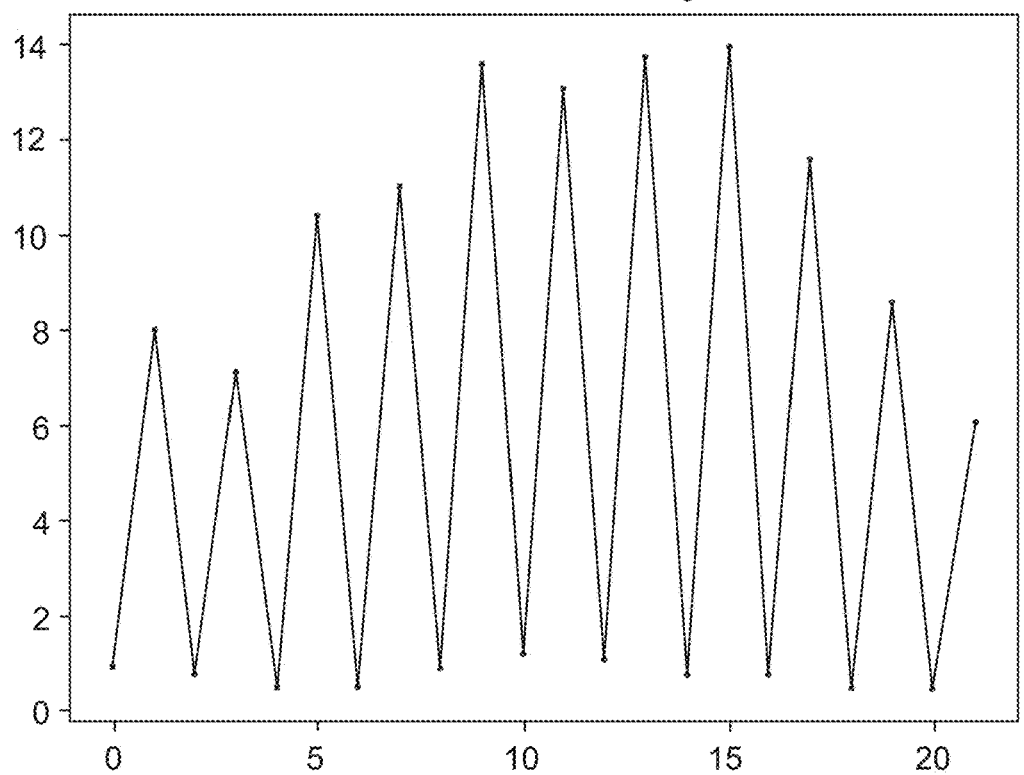
FIG. 8 is a plot of calculated motion score in each image for a 22-slice series of FSE images.
Figure 9:
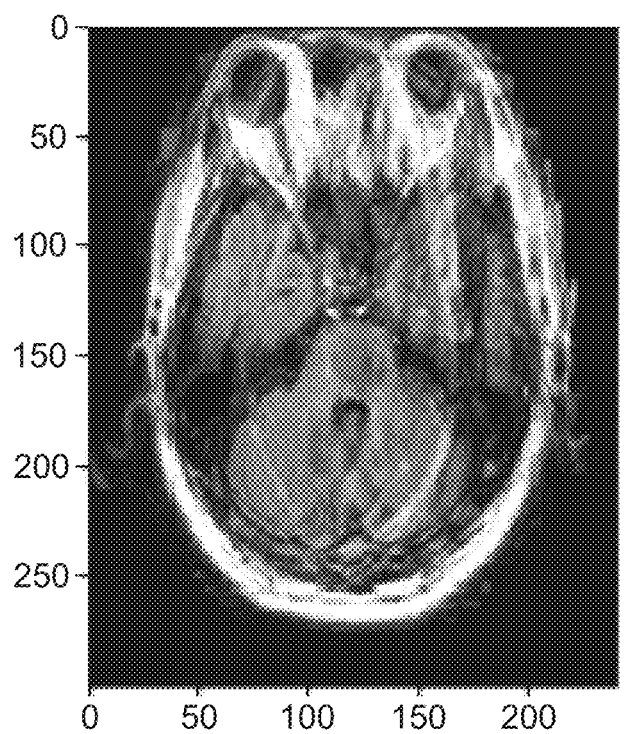
FIG. 9 is an image corresponding to the odd-numbered slices from the 22-slice series of FSE images.
Figure 10:
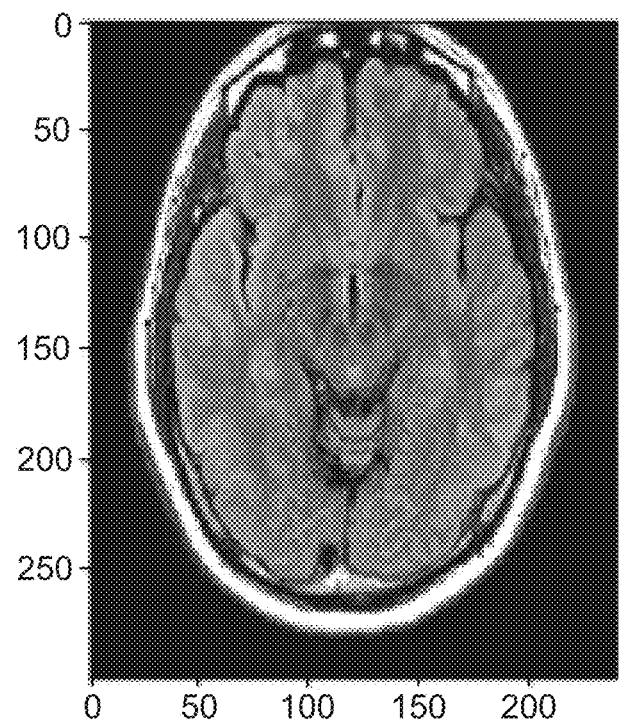
FIG. 10 is an image corresponding to the even-numbered slices from the 22-slice series of FSE images.

FIG. 8 is a plot of calculated motion score in each image for a 22-slice series of FSE images, where the subject was instructed to move his head partway through the scan. Here the odd numbered slices were first acquired in interleaved fashion, then followed by the even numbered slices. More specifically, FIG. 8 is a plot of maximum calculated motion score as a function of image number. FIG. 9 is an image corresponding to the odd-numbered slices, while FIG. 10 is an image corresponds to the even-numbered slices. In comparing FIGS. 9 and 10, the odd slices appear to have motion-related artifacts, while the even slices do not appear to have motion-related artifacts. The difference between the motion scores in the odd and even slices is clearly visible in the plot of FIG. 8.

Figure 11:
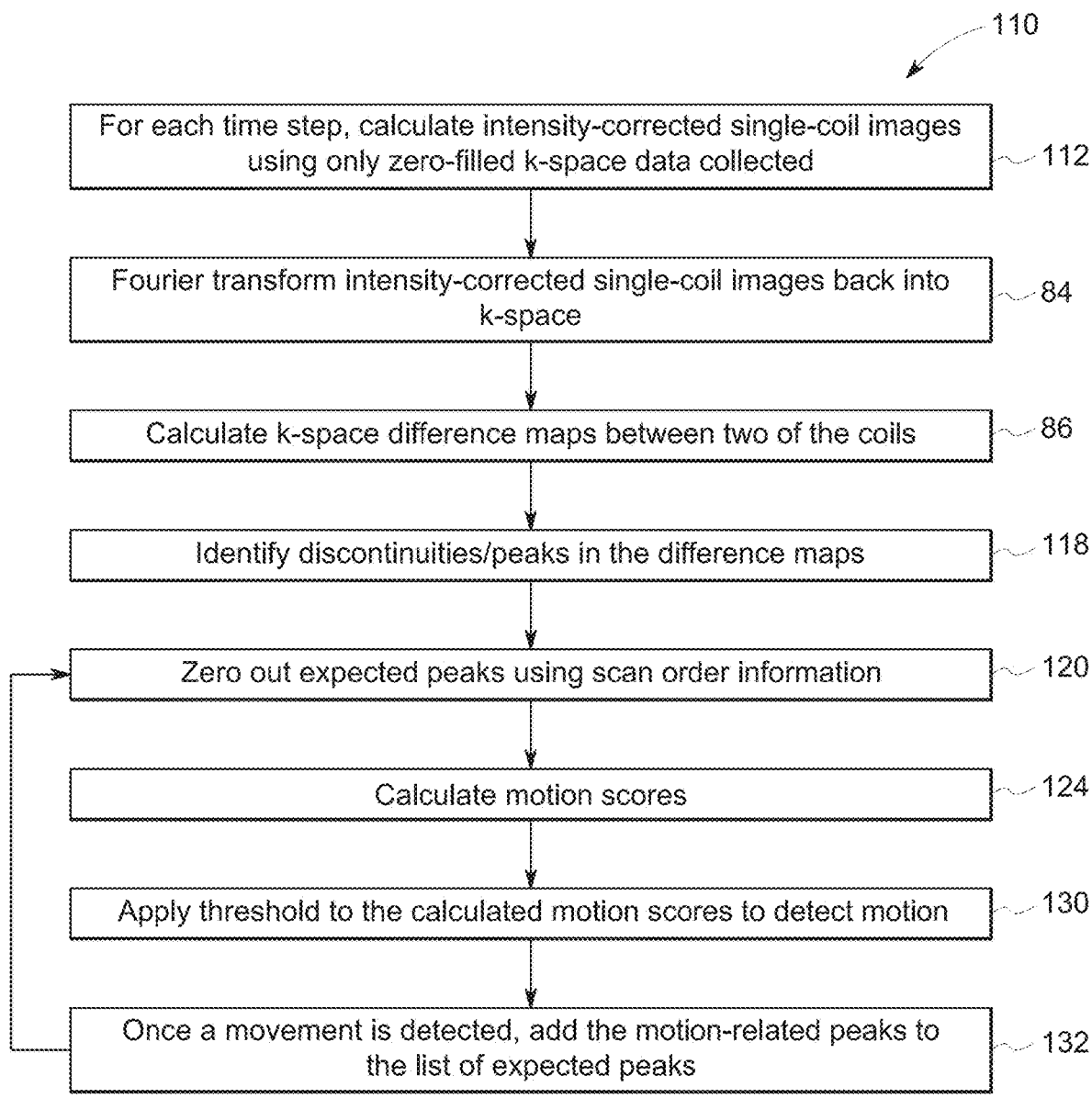
FIG. 11 is a process flow diagram of an embodiment of a method for identifying the occurrence/timing of motion while an MR scan is in progress.

As set forth above, the disclosed embodiments allow motion detection both after the scan of the subject of interest is completed, as well as during scanning. FIG. 11 is a process flow diagram of an embodiment of a method 110 for identifying the occurrence/timing of motion while the scan is in progress. Like the method 80, the method 110 may be performed by the system 10 of FIG. 1, or a remote system having access to the data acquired by system 10. In either case, the method 110 is performed by a general-purpose or application-specific computing system having appropriately configured hardware and software for carrying out the steps described herein. For example, the method 110 may be considered to be performed by a MR motion detection and correction system having processing circuitry and memory circuitry, where the memory circuitry stores instructions (e.g., one or more sets of instructions associated with a software package) that, when performed by the processing circuitry, cause the acts associated with method 110 to be performed. Further, the system that performs method 110 may also include programming to access and/or store the coil data obtained by the system 10 for further processing and analysis.

The method 110 of FIG. 11 includes certain steps that are performed in a similar manner to the method 80 of FIG. 2. However, the data that are input to the method 110 are different in that they are incomplete for most of the scan duration. As set forth in FIG. 11, the method 110 includes, for each time step during the image acquisition, calculating an intensity-corrected single-coil image using only zero-filled k-space data that have already been collected. That is, the acts of block 112 may include taking the Inverse Fourier transform of the raw data from each coil in the array (the data collected as of that time step), multiplying by the conjugate of the coil sensitivity map, and dividing by the absolute value squared of the coil sensitivity map. For regions of k-space that have not been sampled during the scan, those regions of k-space are zero-filled.

Figure 12:
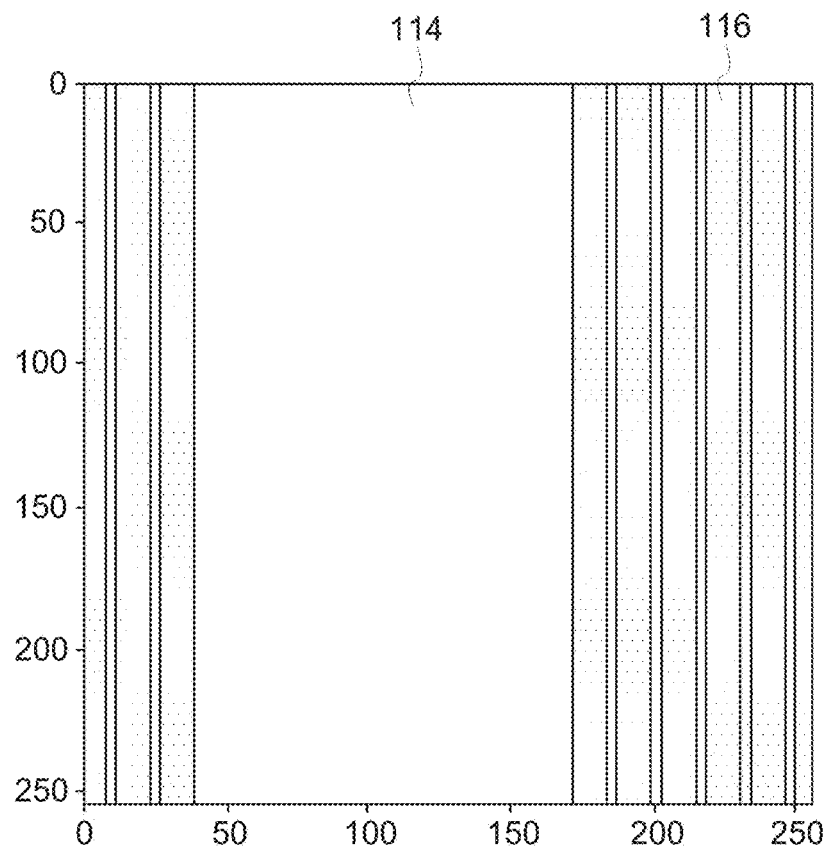
FIG. 12 is a schematic representation of the manner in which k-space is zero-filled according to the method of FIG. 11.

The method 110 then proceeds in a similar manner to the method 80 of FIG. 2, where the single coil images are Fourier transformed (block 84) back into k-space, and k-space difference maps are calculated (block 86) between the data for two coils at a time. This results in the k-space difference between pairs of single-coil images using only the zero-filled k-space data collected up to a particular time step. Referring to FIG. 12, for instance, which is a schematic representation of the manner in which k-space is zero-filled, the k-space data include first sections 114, where k-space is filled with acquired data, and second sections 116, where the k-space region is zero-filled. As shown in FIG. 12, there may be boundaries between the first sections 114 and the second sections 116.

Figure 13:
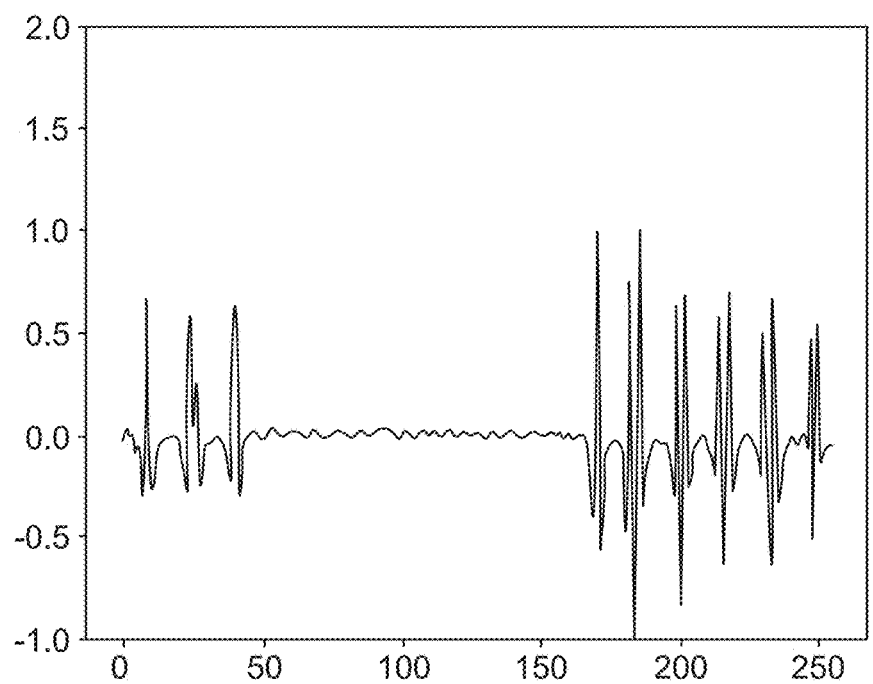
FIG. 13 is a plot of the negative of the second derivative of the signal corresponding to a calculated k-space difference.

Returning to FIG. 11, the method 110 further includes identifying (block 118) discontinuities or peaks in the difference maps or in the difference information. For example, the acts of block 118 may include identifying discontinuities/peaks in the calculated k-space difference by calculating the 1D projection of the absolute value along rows and/or columns and detecting peaks. The peak detection may be performed, for instance, by calculating the negative of the second derivative of the signal at the particular time step, as plotted in FIG. 13.

Figure 14:
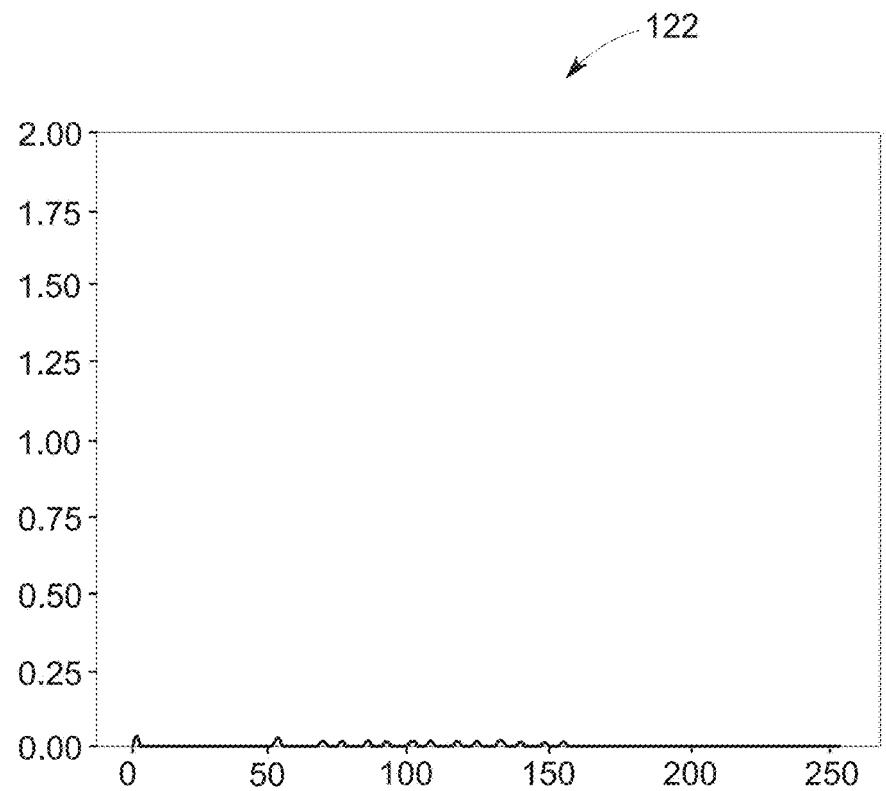
FIG. 14 is an example plot of unexpected peaks produced during the method of FIG. 11 when no motion has occurred.

Once the discontinuities or peaks are identified in accordance with block 118, the method 110 includes zeroing out (block 120) expected peaks using scan order information. For instance, peaks unrelated to motion are generated at any borders between so-far empty (zero-filled regions) and populated regions of k-space. These peaks are removed in accordance with block 120. In the situation shown in FIGS. 11 and 12, no motion has occurred and all peaks result from boundaries between the first sections 114 and the second sections 116. Thus, as shown in FIG. 14, a plot 122 of the "unexpected" positive peaks shows no peaks because no patient motion has occurred.

Figure 15:
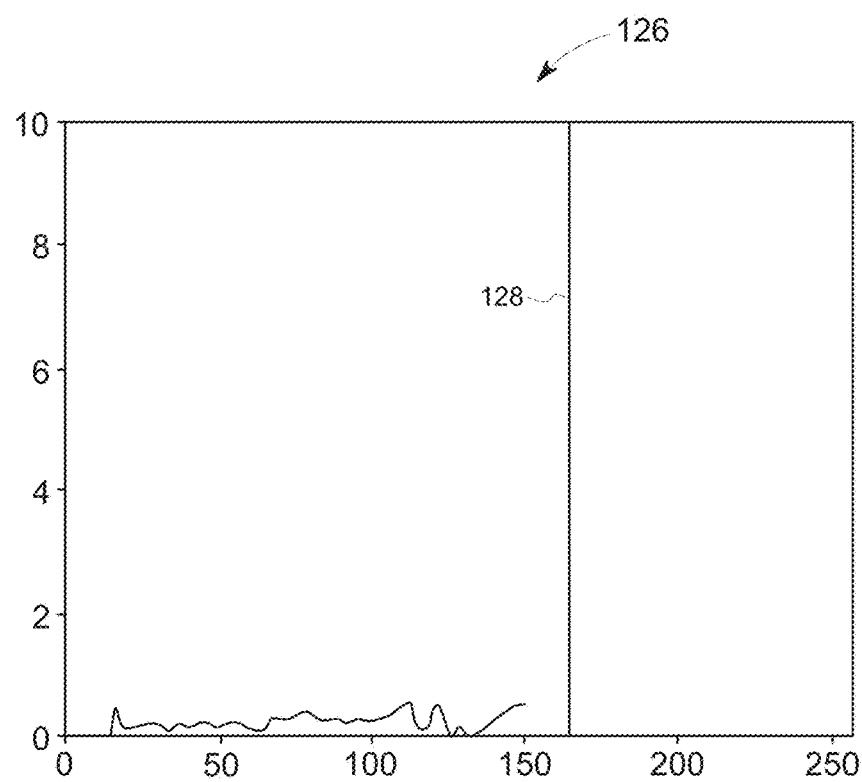
FIG. 15 is an example plot of calculated motion score as a function of time step.

The method 110 includes calculating (block 124) a score for motion. By way of example, calculating the score in accordance with block 124 may include taking the sum of the remaining "unexpected" positive peaks. As shown in FIG. 15, this results in a plot 126 of calculated motion score as a function of time step. Again, because motion does not occur until a time step (noted by line 128) occurring after the time step at which data have been collected, no appreciable peaks show in the plot 126.

In certain embodiments, the unexpected peaks may be normalized. For example, the amplitude of the expected peaks may be used to normalize the unexpected peaks, resulting in the peaks being dimensionless. A natural threshold of about 0.5 may be used in such cases for motion detection. However, the present disclosure is not limited to using 0.5 as a threshold, but it has been found that normalized unexpected peaks above about 0.5 tend to correlate well with the presence of motion.

As there will be non-zero values for the motion score resulting from irregularities that are not a result of motion, the method 110 includes applying a threshold (block 130) to the calculated motion scores to determine whether the calculated motion score is indicative of motion. Thus, motion may be identified if the motion score is at or above the threshold, for example. In the example shown in the motion score plot 126 of FIG. 15, none of the values would be at or above an appropriately selected threshold.

In certain situations, the system performing the method 110 may identify multiple instances of movement. In those situations, additional actions may be performed as part of the method 110. For example, once motion-related peaks are identified, they can be added to the list of expected peaks (block 132). Upon identification of the motion-related peaks in accordance with block 132, the method 110 may cycle back to the acts associated with block 120, were the expected peaks are removed (zeroed out). This may allow for the detection of subsequent motion states by processing of new unexpected peaks (at a later time step).

Figure 16:
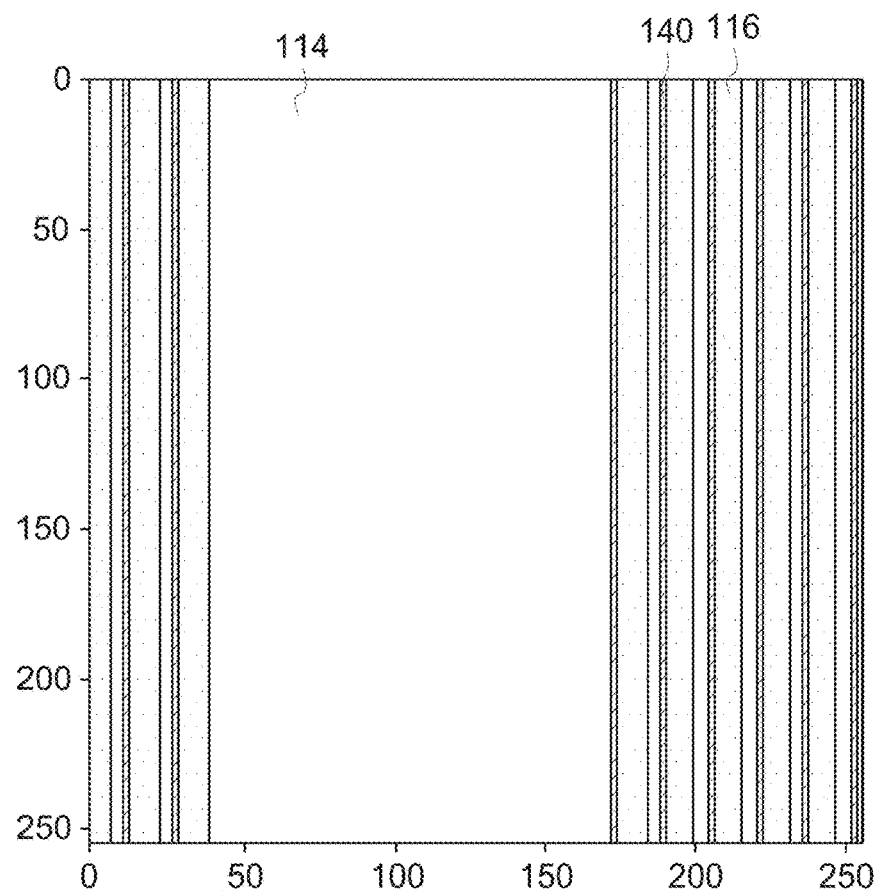
FIG. 16 is a schematic of partially-filled k-space having zero-filled sections, sections filled with data acquired before motion occurred, and sections filled with data acquired after motion occurred.

To help illustrate, FIGS. 16-19 depict various data plots associated with a detected motion event. In particular, FIG. 16 depicts a schematic of partially-filled k-space having the first sections 114, the second sections 116, and third sections 140. In this particular example, the first and third sections 114, 140 represent sections of k-space that are filled with acquired data, but differ in that the first sections 114 are acquired before the motion event, and the third sections 140 are acquired after the motion event. The second sections 116, as previously noted, represent zero-filled sections of k-space.

Figure 17:
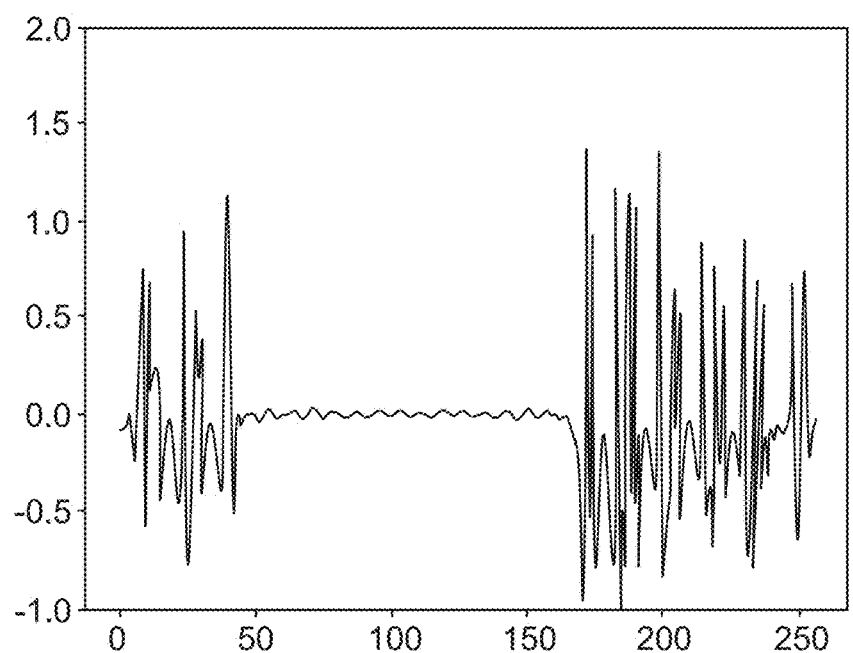
FIG. 17 is a plot of the negative of the second derivative of the signal corresponding to the partially filled k-space.
Figure 18:
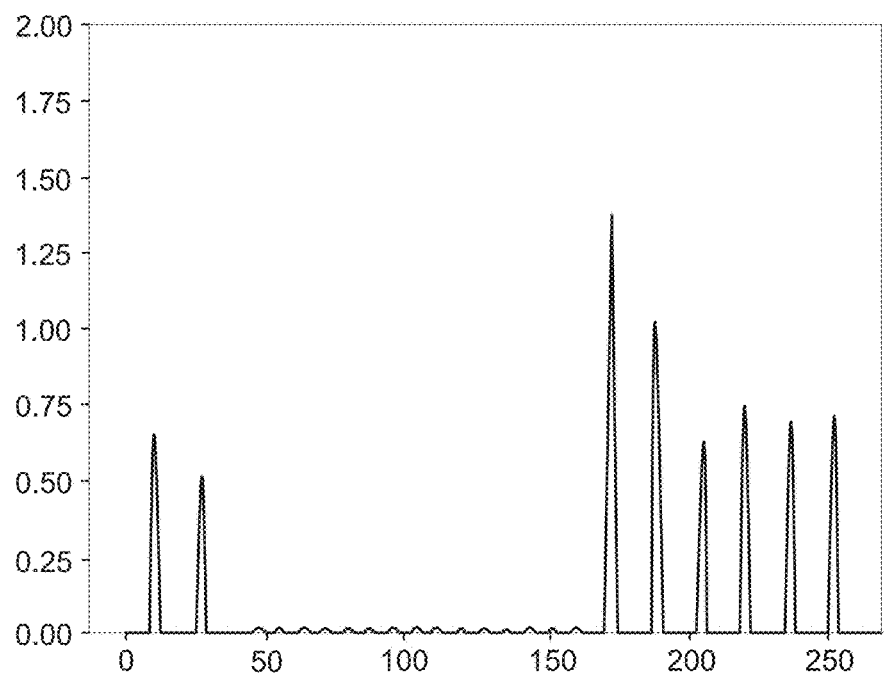
FIG. 18 is a plot of unexpected peaks corresponding to motion and after removal of peaks corresponding to known motion states.
Figure 19:
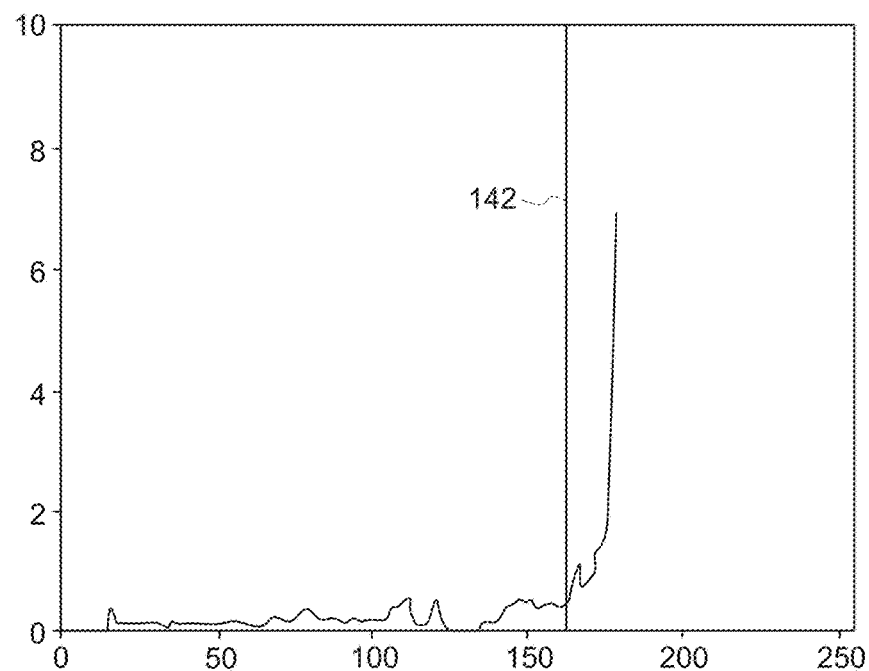
FIG. 19 is an example plot of calculated motion score as a function of time step.

FIG. 17 depicts a plot of the negative of the second derivative of the signal, and includes multiple peaks. Removal of the expected peaks results in the unexpected peak plot depicted in FIG. 18. The graph of FIG. 19 shows the calculated motion score up to the current time step, with the known motion event occurring at a time step denoted by the line 142.

Figure 20:
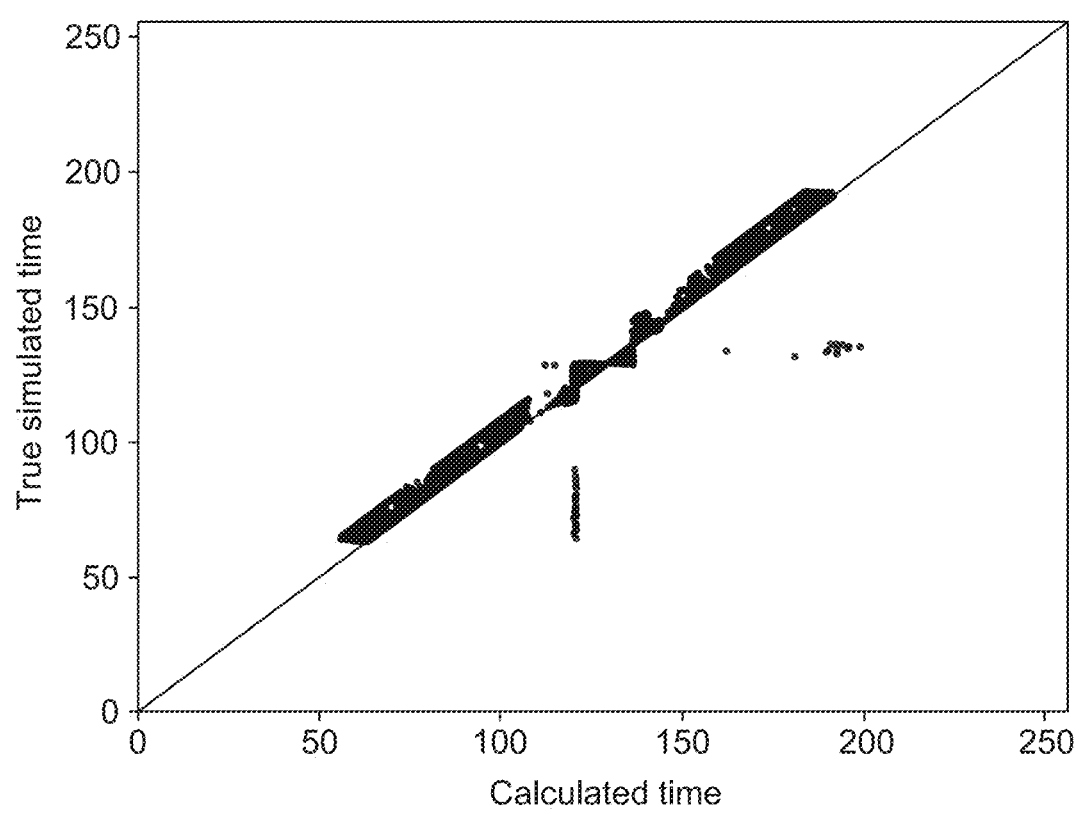
FIG. 20 is a plot, for a simulated data set of MR images, comparing true simulated time of motion versus calculated time of motion determined according to the method of FIG. 11.

The method set forth in FIG. 11 was tested on a simulated data set. The simulated data set included approximately 6500 MR images with randomly selected motion timing and shift. The algorithm ran in an automatic manner on all cases and the true motion timing was compared to the calculated motion timing. A relatively simple motion score was used for calculating the motion timing. The results are shown in FIG. 20. The x values of the points represent the calculated motion timings while the y values represent the true motion timings. As shown, the calculated motion timings very closely matched the simulated true motion timings. The outliers are related to a specific unhandled end case of the calculation and do not represent a limitation of the method.

From the foregoing, it should be appreciated that patient motion during an MR scan sequence creates a composite k-space dataset having a section of k-space acquired before the motion and another section of k-space acquired after the motion (e.g., as shown by the first and third sections 114 and 140 of FIG. 16). In cases where the patient moves multiple times, the k-space dataset may include multiple (e.g., two or more than two) acquired sections, each corresponding to the span of time between patient motion. The Fourier transform of such a composite dataset contains motion artifacts whose severity depends on the timing and size of the motion. Thus, it may be desirable to not only assess whether motion has occurred, but also leverage the information already available from the methods described herein to ascertain the severity of the motion states. For example, the motion score magnitude may be used to determine the severity of a given motion event, vis-à-vis the effect that the motion has on the quality of the images produced from a given scan (or the effect of the motion on sub-images).

Once the motion has been detected and the timing is known, various actions can be taken, including restarting the scan, reacquiring those portions of k-space acquired before the movement, or correcting for the motion to reconstruct an artifact-free MRI image, using the existing data. The manner in which the effects of motion can be mitigated depends on, among other things, the time at which the motion was detected versus the time at which the motion occurred. For example, in situations where motion is not detected until after the scan has been completed, the methods available to ameliorate the effects of the motion may not be the same as those available when the motion is detected during the scan. FIGS. 36-40 detail various methods that may be performed by the MR system 10 in different motion situations.

Figure 21:
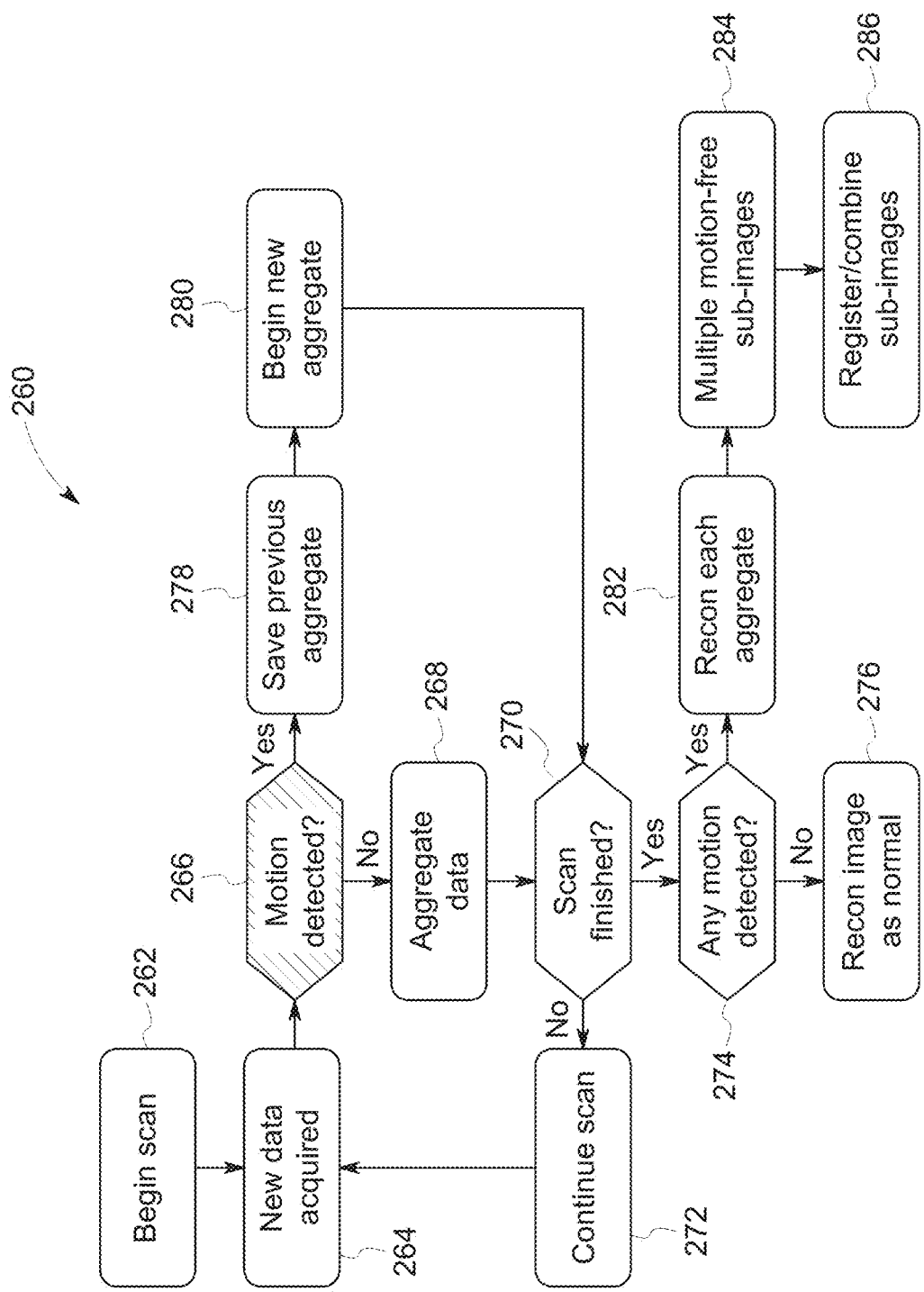
FIG. 21 is an embodiment of an algorithm for performing a scan, monitoring for motion during the scan, and aggregating motion states when motion is detected.

FIG. 21 depicts a process flow diagram of an embodiment of an algorithm 260 performed, for example, by control and analysis circuitry 52, 60 of the MR system 10 in situations where motion is detected during a scan. The algorithm 260 includes various operations, including beginning the scan at operation 262. This begins the process of acquiring new data at operation 264.

Once data have been acquired, the algorithm 260 performs a query 266 to determine whether motion has been detected, using any one or a combination of the methods described herein. If motion has not been detected in the most recent shot, the k-space data are aggregated at operation 268 with the previous k-space data, and if the scan has not finished (query 270), the scan is continued as normal at operation 272. If the scan is finished, another query 274 is performed to determine if motion has been detected and if the scan is motion-free, the image is reconstructed according to conventional techniques.

If, at query 266, motion is detected, the data previously collected are saved as one motion state at operation 278, and a new motion state is started at operation 280. The new motion state initially includes only the most recent k-space data collected. As the scan continues, k-space data will be aggregated to this motion state as long as further motion is not detected. The results of the operations described to this point result in continuing to either add to the current motion state or creating new motion states until the scan is complete.

At query 274, if there were multiple motion states, each aggregate (each set of k-space data corresponding to a single motion state) is separately reconstructed at operation 282. In this respect, each reconstructed motion state results in a motion-free sub-image and multiple motion-free sub-images 284 are produced.

At operation 286, various known techniques can be used to combine the different sub-images, or to separately reconstruct them into full images. For example, the sub-images 284 can be registered and combined to create a motion-free image, through methods known in the art. Or the k-space data from each motion state can be reconstructed using parallel imaging, compressed sensing, or a sparse-reconstruction neural network. The resulting images can then be registered and combined, through methods known in the art. As one example, operation 286 may include joint iterative estimation of motion and image, with timing constraints. The timing constraints (i.e., motion timing) are obtained based on the neural network predictions.

Figure 22:
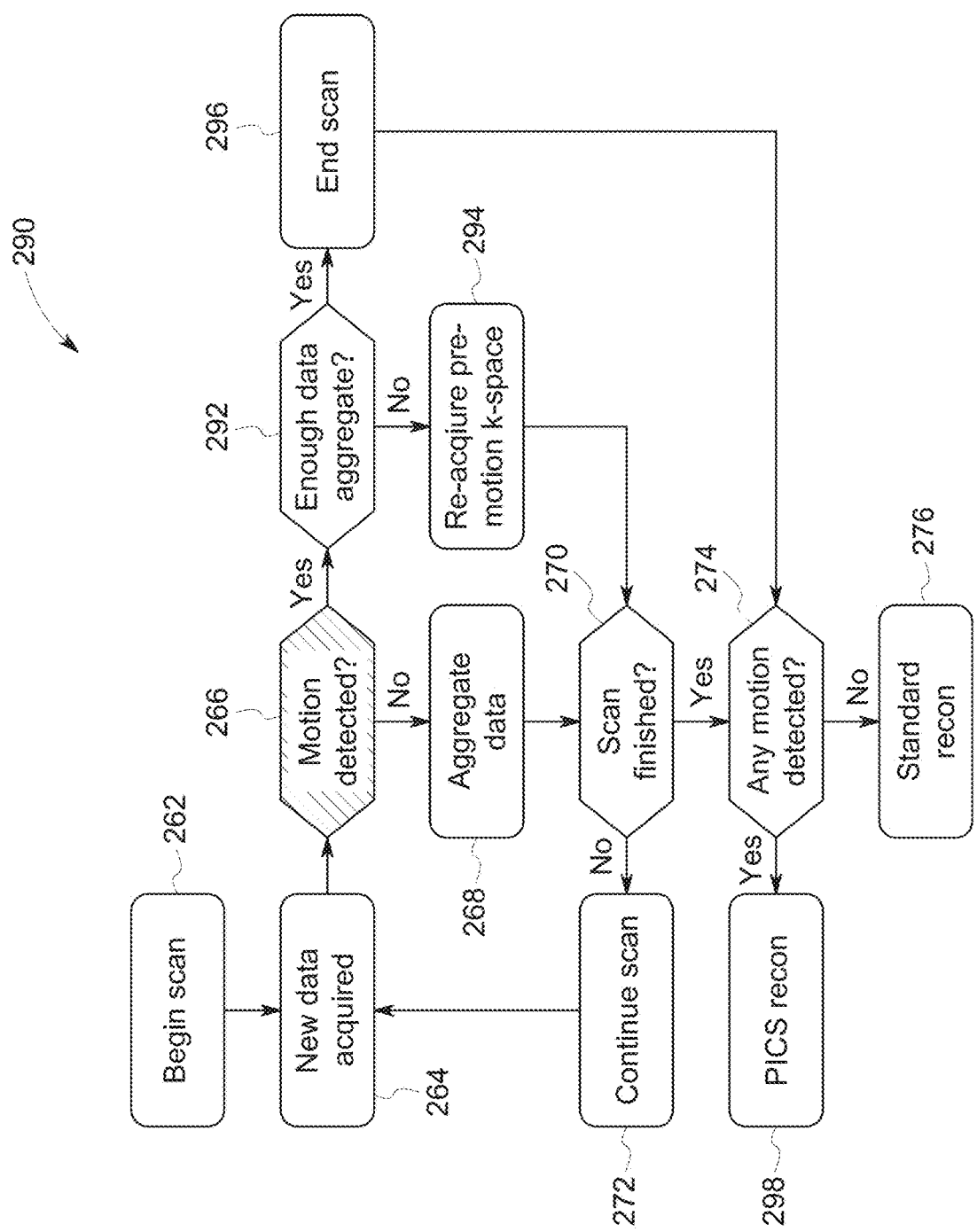
FIG. 22 is an embodiment of an algorithm for performing a scan, monitoring for motion during the scan, and aggregating a final motion state when motion is detected.

Using a similar sequence, instead of aggregating the separate motion states, the k-space data may be adaptively reacquired as shown in FIG. 22. In particular, algorithm 290 of FIG. 22 includes many of the same operations as the algorithm 260 of FIG. 21, including operations 262, 264, 268, 272, and 276 as well as queries 266, 270, and 274.

For the algorithm 290, if motion is detected at query 266, then the system (e.g., control and analysis circuitry 52, 60) determines whether enough of k-space has been filled to make possible parallel imaging/compressed sensing (PICS) or use of a sparse-image-reconstruction neural network at query 292.

If not enough of k-space has been filled, then the algorithm 290 continues to acquire data by adding data to a new motion state at operation 294. If necessary, lines of k-space filled in during previous motion states are re-acquired. Previous motion state data may be discarded or used for other purposes.

Once enough of k-space has been filled to make parallel imaging or sparse image reconstruction possible, the scan is ended at operation 296. The final image is reconstructed at operation 298 with just the portion of k-space acquired in the final motion state using one of the aforementioned reconstruction algorithms (e.g., PICS recon or a sparse-image-reconstruction neural network).

Figure 23:
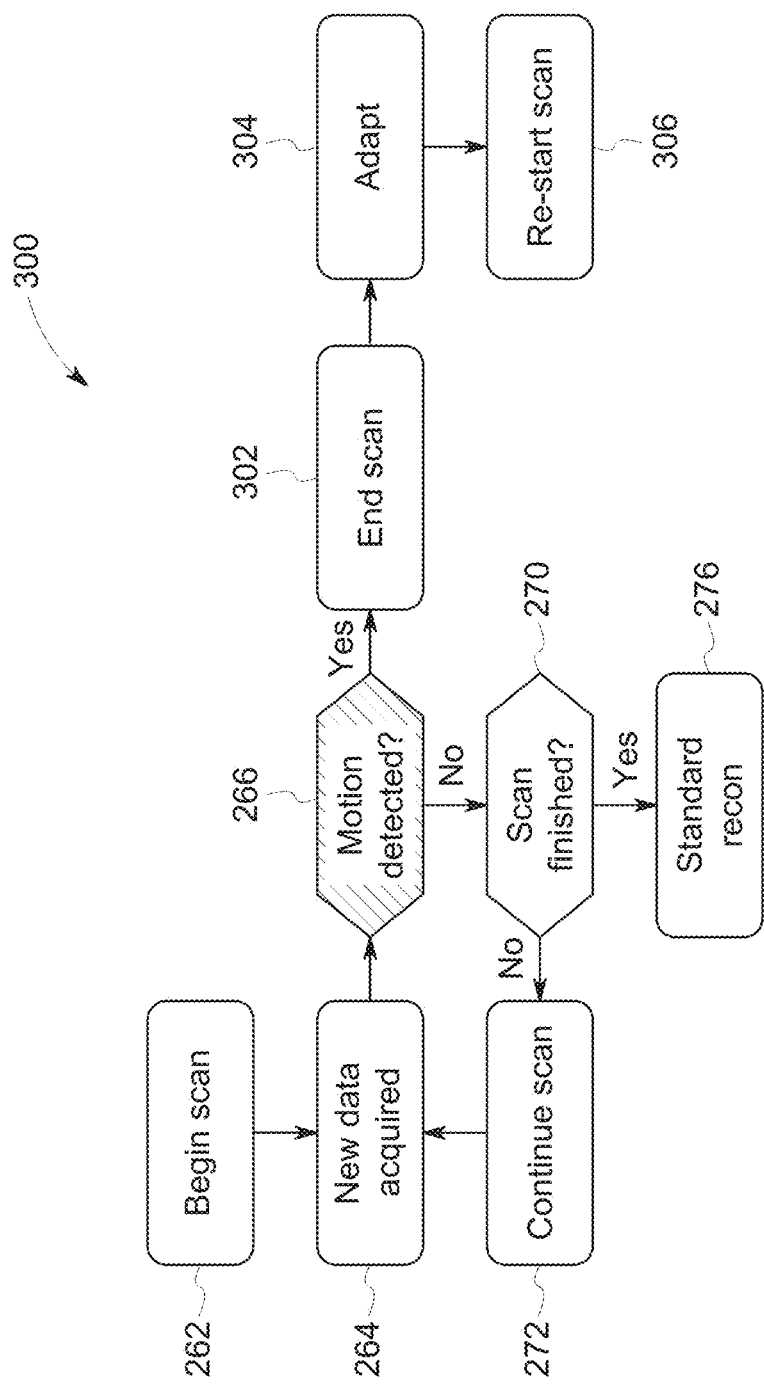
FIG. 23 is an embodiment of an algorithm for performing a scan, monitoring for motion during the scan, and adapting to the motion during the scan when motion is detected.

In certain embodiments, the detected motion may be so severe that the data are essentially unusable. FIG. 23 depicts an embodiment of an algorithm 300 that involves ending the scan early if motion is detected. For example, the algorithm 300 may include many of the operations and queries described previously with respect to FIGS. 36 and 37, except that once severe motion is detected at query 266, the scan is ended at operation 302. For example, the motion score predicted by the CNN 180 may be so high that the motion may be considered severe and the scan ended.

Ending the scan in this manner allows an operator to take adaptive actions at operation 304. For example, the operator may instruct the subject to remain still, assist the subject if remaining still is difficult, or a more motion-robust imaging sequence may be utilized (e.g., automatically chosen by the system). Once adaptive correction is performed, the scan may be re-started at operation 306.

The algorithm 300 may be used in combination with the two algorithms 260, 290 described above, by taking advantage of the fact that the motion score reflects not only the presence but also severity of motion. For instance, the scan can be ended early if severe motion is detected multiple times, but otherwise one of the other algorithms can be implemented in response to a smaller motion score. This algorithm 300 also makes use of the quality score to allow selection of a particular tolerance for motion scores. For instance, depending on the intended use for the finished scans, minor motion artifacts may not affect the diagnosis. The same neural network with a dynamic threshold allows multiple thresholds to be customized to specific applications.

Figure 24:
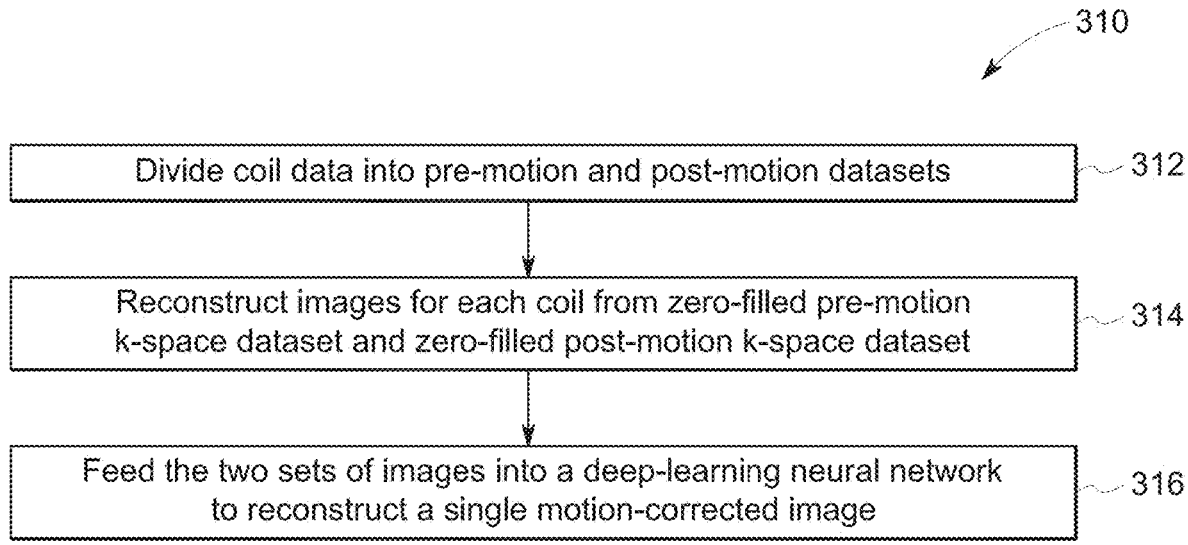
FIG. 24 is an embodiment of a method of reconstructing a motion-free image from motion-corrupted datasets.

Disclosed embodiments also include methods for image reconstruction when motion has occurred. For example, FIGS. 39 and 40 both depict embodiments of methods that can be used to reconstruct a motion artifact-free image. FIG. 24, in particular, is a method 310 for reconstructing a motion artifact-free image by first dividing coil data (block 312) into pre-motion and post-motion datasets. For example, using the scan order and the timing of when the motion occurred, the coils' k-space data is broken into two sets. The first set includes the parts of k-space that were scanned before the subject movement occurred and the second set the data after the movement occurred.

After the coil data are divided, for each coil two images are reconstructed (block 314). The first image is reconstructed using the zero-filled k-space data collected before the movement occurred, and the second image is reconstructed using the zero filled k-space data collected after the movement. In method 310, the two sets of images for each coil are fed (block 316) into a deep-learning neural network that reconstructs a single motion-corrected image.

Figure 25:
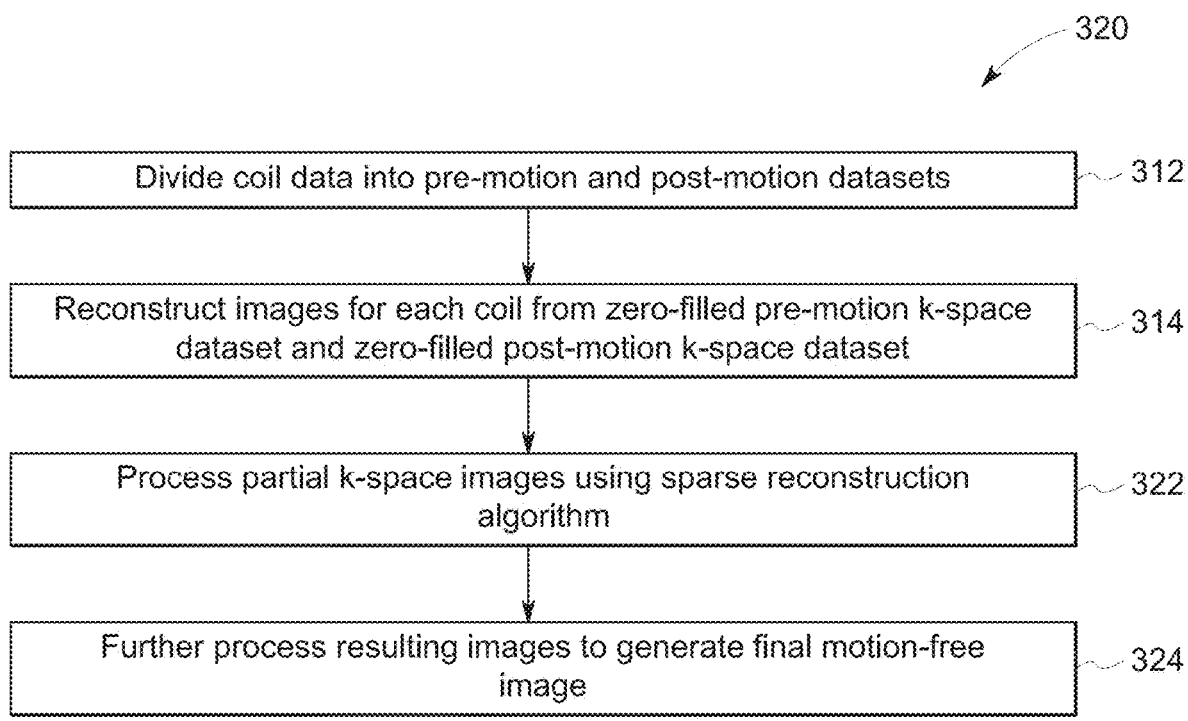
FIG. 25 is another embodiment of a method of reconstructing a motion-free image from motion-corrupted datasets.

Method 320, on the other hand and as depicted in FIG. 25, includes the acts represented by blocks 312 and 314, but instead the partial k-space images are each processed using a sparse reconstruction algorithm (block 322). The images resulting from the sparse reconstruction algorithm may then be further processed and combined, or fed to a neural network to generate a final motion-free image (block 324).

Technical effects of the invention include automatic detection and timing of patient movement, and mitigation of the effects of the patient movement on an overall MR scan. Remedial actions may include restarting the scan, reacquiring those portions of k-space acquired before the movement, or correcting for the motion using the existing data. In this way, the motion detection and correction techniques described herein may improve the throughput of MRI machines, improve the patient experience and reduce burden on MR technicians.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A magnetic resonance imaging method comprising:
    generating intensity-corrected single-coil images from raw magnetic resonance (MR) data of an imaged subject, wherein the raw MR data comprise data collected by each coil of a plurality of coils in a receiving coil array of an MR system, and wherein the raw MR data are associated with a scan order used during acquisition thereof, the scan order having a plurality of time steps in which k-space is filled in a predetermined manner;
    identifying inconsistencies among the intensity-corrected single-coil images;
    calculating, for at least one time step of the scan order, a motion score using the scan order and the inconsistencies to identify timing associated with motion occurring during the acquisition; and
    performing a corrective action based at least on the timing associated with the motion to ameliorate the effects of the motion on an MR image produced using at least a portion of the raw MR data.

2. The method of claim 1, wherein identifying inconsistencies among the intensity-corrected single-coil images comprises:
    applying a Fourier transform to the intensity-corrected single-coil images to transform image data of the intensity-corrected single-coil images into k-space data; and
    determining differences between the k-space data of pairs of intensity-corrected single-coil images.

3. The method of claim 2, wherein determining differences between the k-space data of pairs of intensity-corrected single-coil images comprises taking an absolute difference between the Fourier transform of two intensity-corrected single-coil images.

4. The method of claim 2, wherein determining differences between the k-space data of pairs of intensity-corrected single-coil images comprises generating a k-space difference map representing a difference between the k-space data for a pair of the intensity-corrected single-coil images.

5. The method of claim 4, wherein identifying inconsistencies between the intensity-corrected single-coil images comprises identifying locations of relatively bright columns or rows in the k-space difference map.

6. The method of claim 4, wherein identifying inconsistencies among the intensity-corrected single-coil images comprises projecting the k-space difference map along the readout direction onto an axis to produce a plot of integrated k-space difference as a function of phase-encoding index, and identifying peaks that are relatively larger than others, and wherein a size of a peak is proportional to a degree of inconsistency.

7. The method of claim 6, wherein calculating, for the at least one time step of the scan order, the motion score comprises integrating over all previous time steps the peaks of the plot of integrated k-space difference.

8. The method of claim 1 wherein k-space is undersampled to accelerate imaging, by use of parallel imaging, compressed sensing, or some other method.

9. The method of claim 1, comprising, for the at least one time step of the scan order, zero-filling regions of k-space in the raw MR data that have not yet been sampled such that the raw MR data comprise regions of k-space that are zero-filled.

10. The method of claim 9, comprising determining differences between k-space data of pairs of intensity-corrected single-coil images by generating a k-space difference map by taking an absolute difference between the Fourier transform of two intensity-corrected single-coil images using only the zero-filled k-space data collected up to a particular time step.

11. The method of claim 10, wherein identifying inconsistencies between the intensity-corrected single-coil images comprises identifying peaks in the calculated k-space difference by calculating a 1D projection of the absolute value along rows or columns of k-space, and detecting peaks.

12. The method of claim 11, wherein detecting peaks comprises calculating the negative of the second derivative of the signal at the time step.

13. The method of claim 12, wherein calculating the motion score, for the at least one time step of the scan order, comprises:
removing peaks that are due to borders between sampled and unsampled locations of k-space according to scan order information; and
calculating the motion score by taking a sum of the remaining peaks.

14. The method of claim 13, wherein the motion score is calculated using the amplitude of the removed peaks to normalize the remaining peaks.

15. The method of claim 13, comprising applying a threshold to the calculated motion score to determine whether the calculated motion score is indicative of motion.

16. The method of claim 1, wherein performing the corrective action comprises reacquiring portions of k-space acquired before movement.

17. The method of claim 1, wherein performing the corrective action comprises correcting for the motion using the existing raw MR data using a deep-learning neural network or iterative optimization.

18. A magnetic resonance imaging (MRI) method comprising:
generating intensity-corrected single-coil images from raw magnetic resonance (MR) data of an imaged subject, wherein the raw MR data comprise data collected by each coil of a plurality of coils in a receiving coil array of an MRI system;
identifying inconsistencies among the intensity-corrected single-coil images;
identifying whether motion occurred during acquisition of the raw MR data based at least on the inconsistencies; and
performing further operations of the MRI system in response to determining that motion occurred during the acquisition.

19. The method of claim 18, wherein performing further operations of the MRI system in response to determining that motion occurred during the acquisition comprises restarting an MR scan to re-acquire raw MR data of the imaged subject.

20. The method of claim 18, wherein identifying inconsistencies among the intensity-corrected single-coil images comprises:
applying a Fourier transform to the intensity-corrected single-coil images to transform image data of the intensity-corrected single-coil images into k-space data;
determining differences between the k-space data of pairs of intensity-corrected single-coil images;
calculating motion scores for at least some time steps of a scan order associated with acquisition of the raw MR data based at least on the determined differences, the scan order defining phase encode as a function of time step; and
identifying presence and timing of motion based on the calculated motion scores.

21. The method of claim 20, wherein performing further operations of the MRI system in response to determining that motion occurred during the acquisition comprises reacquiring portions of k-space acquired before movement.

22. A magnetic resonance imaging (MRI) method comprising:
obtaining raw magnetic resonance (MR) data of a subject, wherein the raw MR data comprises data collected by each coil of a plurality of coils in a receiving coil array of an MRI system, and wherein the raw MR data is associated with a scan order used during acquisition thereof, the scan order having a plurality of time steps in which k-space is filled in a predetermined manner;
using inconsistencies among calculated intensity-corrected single-coil images produced from the raw MR data to detect motion of the subject and, together with the scan order, determine the timing of the motion during the acquisition; and
performing image reconstruction using the timing of the motion to generate a single motion-corrected image.

23. The method of claim 22 comprising:
dividing the data collected by each coil of the plurality of coils coil data into pre-motion and post-motion datasets based on the timing;
reconstructing images for each coil from zero-filled pre-motion k-space dataset and zero-filled post-motion k-space dataset; and
providing the two sets of images as inputs into a deep-learning neural network to reconstruct the single motion-corrected image.

* * * * *